US009861712B2

(12) United States Patent
Hyeon et al.

(10) Patent No.: US 9,861,712 B2
(45) Date of Patent: Jan. 9, 2018

(54) PREPARATION OF EXTREMELY SMALL AND UNIFORM SIZED, IRON OXIDE-BASED PARAMAGNETIC OR PSEUDO-PARAMAGNETIC NANOPARTICLES AND MRI T1 CONTRAST AGENTS USING THE SAME

(75) Inventors: Taeg Hwan Hyeon, Seoul (KR); Byung Hyo Kim, Seoul (KR); No Hyun Lee, Daejeon (KR); Eung Gyu Kim, Daejeon (KR); Bong Sik Jeon, Daejeon (KR); Eun Byul Kwon, Daejeon (KR); Ju Young Park, Daejeon (KR); Wan Jae Myeong, Daejeon (KR)

(73) Assignee: Hanwha Chemical Corporation, Seoul (KR)

(*) Notice: Subject to any disclaimer, the term of this patent is extended or adjusted under 35 U.S.C. 154(b) by 908 days.

(21) Appl. No.: 13/814,036

(22) PCT Filed: Aug. 5, 2011

(86) PCT No.: PCT/KR2011/005746
§ 371 (c)(1),
(2), (4) Date: Feb. 4, 2013

(87) PCT Pub. No.: WO2012/018240
PCT Pub. Date: Feb. 9, 2012

(65) Prior Publication Data
US 2013/0164222 A1    Jun. 27, 2013

(30) Foreign Application Priority Data

Aug. 5, 2010  (KR) .................. 10-2010-0075523
Aug. 3, 2011  (KR) .................. 10-2011-0077534

(51) Int. Cl.
*A61K 49/18* (2006.01)
*A61K 49/10* (2006.01)
*B82Y 5/00* (2011.01)

(52) U.S. Cl.
CPC .......... *A61K 49/1839* (2013.01); *A61K 49/10* (2013.01); *A61K 49/186* (2013.01); *A61K 49/1836* (2013.01); *A61K 49/1842* (2013.01); *A61K 49/1845* (2013.01); *B82Y 5/00* (2013.01); *Y10S 977/811* (2013.01); *Y10S 977/882* (2013.01); *Y10S 977/93* (2013.01); *Y10T 428/2982* (2015.01)

(58) Field of Classification Search
CPC ............ A61K 49/1836; A61K 49/1839; A61K 49/1842; A61K 49/1845; A61K 49/186; Y10T 428/2982; Y10S 977/882; Y10S 977/811; Y10S 977/93; B82Y 5/00
See application file for complete search history.

(56) References Cited

U.S. PATENT DOCUMENTS

| 5,160,725 A | 11/1992 | Pilgrimm |
| 6,638,494 B1 | 10/2003 | Pilgrimm |
| 6,962,685 B2 | 11/2005 | Sun |
| 8,696,795 B2 | 4/2014 | Hilbig |
| 8,828,357 B2 | 9/2014 | Lee et al. |
| 2006/0133990 A1* | 6/2006 | Hyeon ............. B22F 9/30 423/622 |
| 2006/0211152 A1* | 9/2006 | Peng ............. C01G 15/00 438/3 |
| 2008/0245186 A1* | 10/2008 | Yang ............. B22F 9/24 75/362 |
| 2009/0324494 A1 | 12/2009 | Ham et al. |
| 2011/0020243 A1 | 1/2011 | Aydogan |
| 2011/0165086 A1 | 7/2011 | Lee et al. |
| 2013/0045160 A1 | 2/2013 | Ham et al. |
| 2013/0164222 A1 | 6/2013 | Hyeon et al. |

FOREIGN PATENT DOCUMENTS

| JP | 2663976 B2 | 6/1997 |
| JP | 2000507197 A | 6/2000 |
| JP | 200443287 A | 2/2004 |
| JP | 2006104051 A | 4/2006 |
| JP | 2008521591 A | 6/2008 |
| JP | 2008169110 A | 7/2008 |
| JP | 2008221207 A | 9/2008 |
| JP | 2009531296 A | 9/2009 |

(Continued)

OTHER PUBLICATIONS

Coey, J. M. D., Noncollinear Spin Arrangement in Ultrafine Ferrimagnetic Crystallites, Physical Review Letters, 1971, 1140-1142, 27.
Corot, Claire et al., Recent Advances in Iron Oxide Nanocrystal Technology for Medical Imaging, Advanced Drug Delivery Reviews, 2006, 1471-1504, 58.
Gupta, A. K. & Gupta, M., Synthesis and Surface Engineering of Iron Oxide Nanoparticles for Biomedical Applications, Biomaterials, 2005, 3995-4021, 26.
Jun, Y.-W. et al., Nanoscale Size Effect of Magnetic Nanocrystals and Their Utilization for Cancer Diagnosis via Magnetic Resonance Imaging, J. Am. Chem. Soc., 2005, 5732-5733, 127.
Limbach, L. K. et al., Exposure of Engineered Nanoparticles to Human Lung Epithelial Cells: Influence of Chemical Composition and Catalytic Activity on Oxidative Stress, Environmental Science & Technology, 2007, 4158-4163, 41.

(Continued)

*Primary Examiner* — Michael G Hartley
*Assistant Examiner* — Leah Schlientz
(74) *Attorney, Agent, or Firm* — The Webb Law Firm

(57) ABSTRACT

Provided are a preparation method of iron oxide-based paramagnetic or pseudo-paramagnetic nanoparticles, iron oxide-based nanoparticles prepared by the same, and a T1 contrast agent including the same. More particularly, the disclosure describes a method for preparation of iron oxide nanoparticles having a extremely small and uniform size of 4 nm or less based on thermal decomposition of iron oleate complex, iron oxide-based paramagnetic or pseudo-paramagnetic nanoparticles prepared by the same, and a T1 contrast agent including iron oxide-based paramagnetic or pseudo-paramagnetic nanoparticles.

5 Claims, 19 Drawing Sheets

(56) References Cited

FOREIGN PATENT DOCUMENTS

| JP | 2010512463 A | 4/2010 |
|---|---|---|
| JP | 2013514123 A | 4/2013 |
| KR | 100686206 B1 | 2/2007 |
| KR | 1020110080781 A | 7/2011 |
| WO | 2007097593 A1 | 8/2007 |
| WO | 2008121438 A2 | 10/2008 |
| WO | 2012018240 A2 | 2/2012 |

OTHER PUBLICATIONS

Linderoth, S. & Hendriksen, P. V., on Spin-Canting in Maghemite Particles, J. Appl. Phys., 1994, 6583-6585, 75, 10.

Marco, M. D. et al., Physicochemical Characterization of Ultrasmall Superparamagnetic Iron Oxide Particles (USPIO) for Biomedical Application as MRI Contrast Agents, International Journal of Nanomedicine, 2007, 609-622, 2, No. 4.

Na, H. B. et al., Development of a T1 Contrast Agent for Magnetic Resonance Imaging Using MnO Nanoparticles, Angew Chem. Int. Ed., 2007, 5397-5401, 46.

Park, Jognam et al., Ultra-large-scale Syntheses of Monodisperse Nanocrystals, Nature Materials, Dec. 2004,891-895, 3.

Qiao, R. et al., Superparamagnetic Iron Oxide Nanoparticles: from Preparations to in Vivo MRI Applications, Journal of Materials Chemistry, 2009, 6274-6293, 19.

Sahoo, Y. et al., Alkyl Phosphonate/Phosphate Coating on Magnetite Nanoparticles: A Comparison with Fatty Acids, Langmuir, 2001, 7907-7911, 17.

Taboada, E. et al., Relaxometric and Magnetic Characterization of Ultrasmall Iron Oxide Nanoparticles with High Magnetization. Evaluation as Potential T1 Magnetic Resonance Imaging Contrast Agents for Molecular Imaging, Langmuir, 2007, 4583-4588, 23.

Teng, Xiaowei & Yang, Hong, Effects of Surfactants and Synthetic Conditions on the Sizes and Self-assembly of Monodisperse Iron Oxide Nanoparticles, Journal of Materials Chemistry, 2004, 774-779, 14.

Tromsdorf, U. I. et al., A Highly Effective, Nontoxic T1 MR Contrast Agent Based on Ultrasmall PEGylated Iron Oxide Nanoparticles, Nano Letters, 2009, 4434-4440, 9, 12.

Park et al., Transformation of hydrophobic iron oxide nanoparticles to hydrophilic and biocompatible maghemite nanocrystals for use as highly efficient MRI contrast agent, Journal of Materials Chemistry, Mar. 16, 2011, pp. 11472-11477, vol. 21.

Chih-Jung Chen et al., "Preparation of Monodisperse Iron Oxide Nanoparticles via the Synthesis and Decomposition of Iron Fatty Acid Complexes", Nanoscale Res Lett, 2009, 1343-1350, vol. 4.

Sun et al., "Size-Controlled Synthesis of Magnetite Nanoparticles," J. Am. Chem. Soc., 2002, pp. 8204-8205, vol. 124.

Sigovan et al., "Rapid-Clearance Iron Nanoparticles for Inflammation Imaging of Atherosclerotic Plaque: Initial Experience in Animal Model", Radiology, Aug. 2009, pp. 401-409, vol. 252, No. 2.

* cited by examiner

[Figure 1]
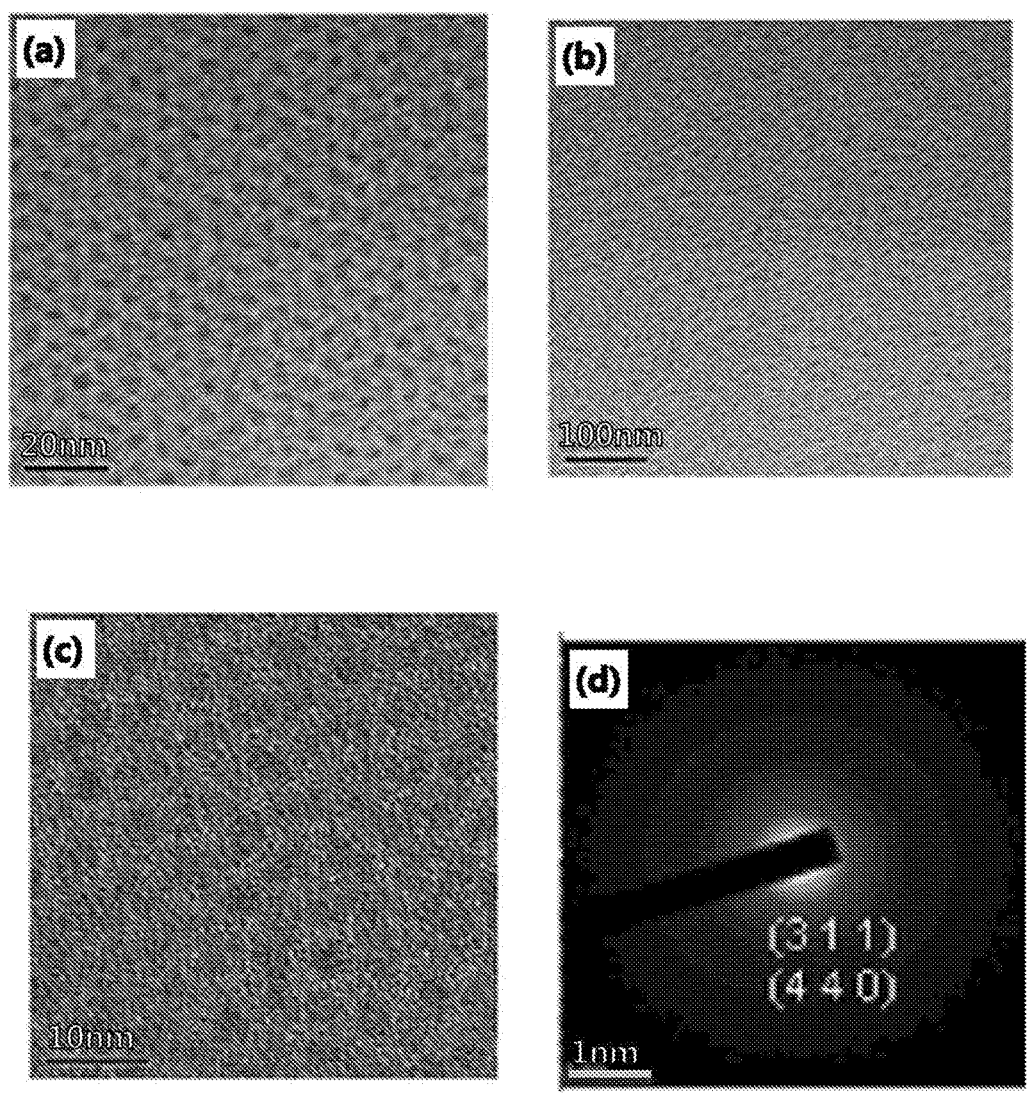

[Figure 2]
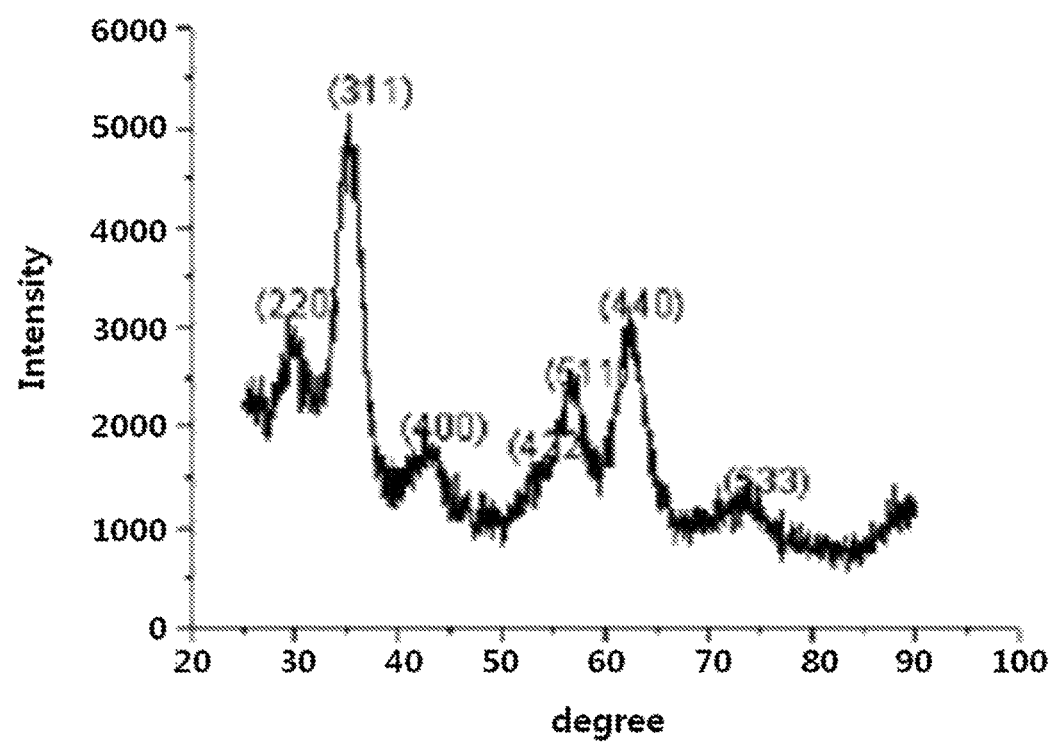

【Figure 3】
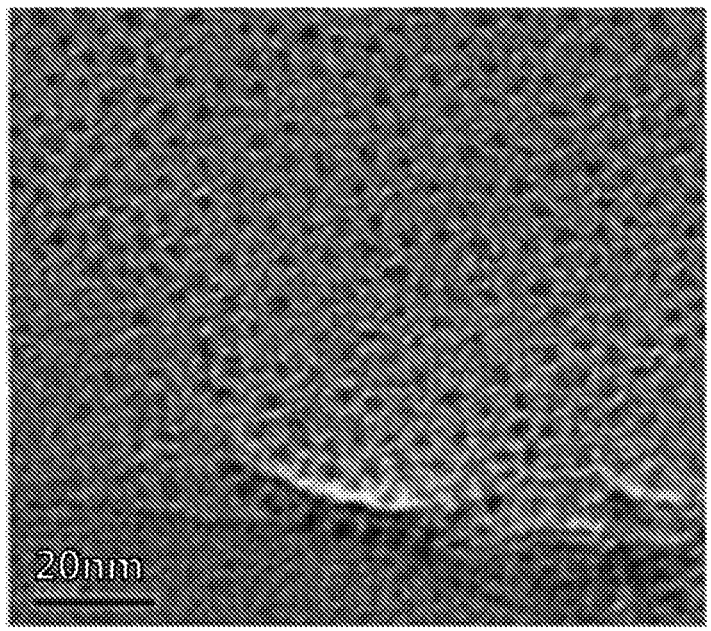
【Figure 4】
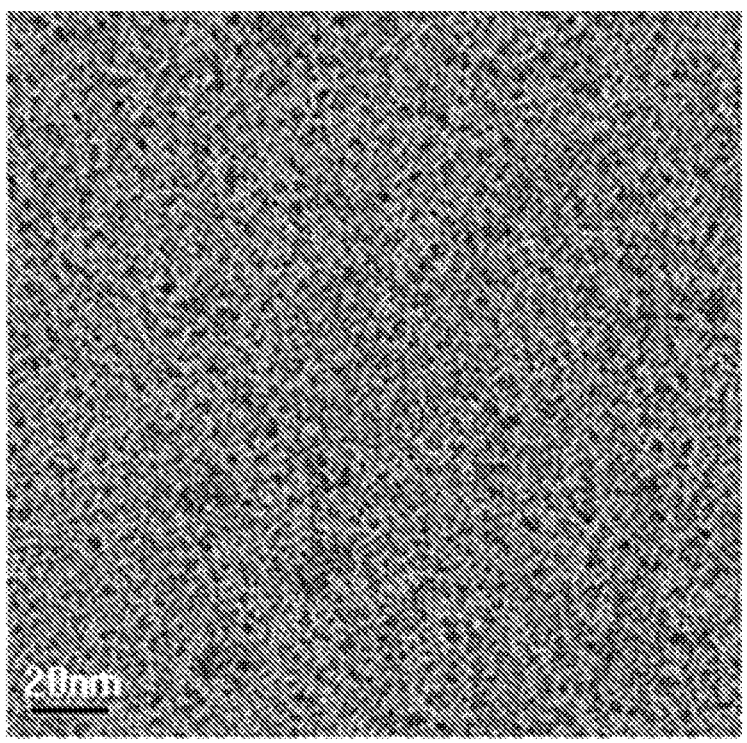

【Figure 5】
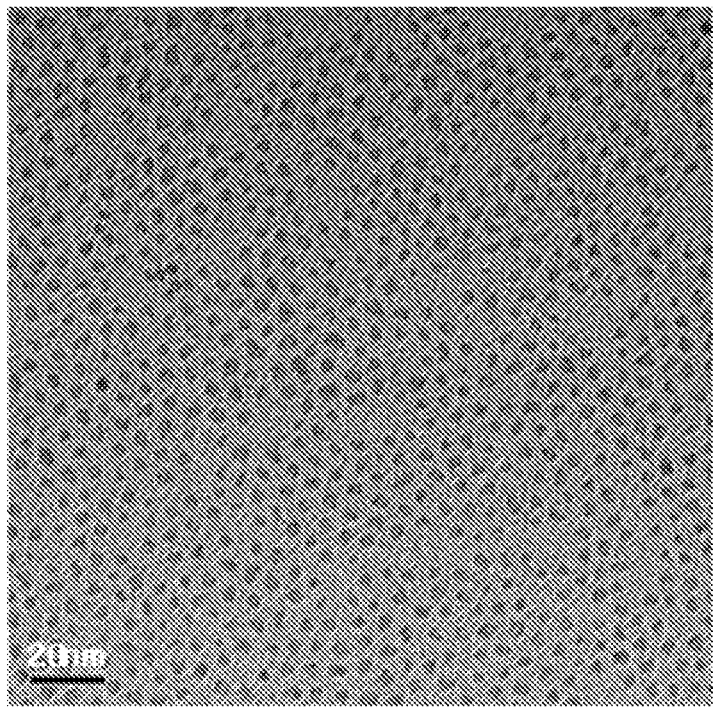
【Figure 6】
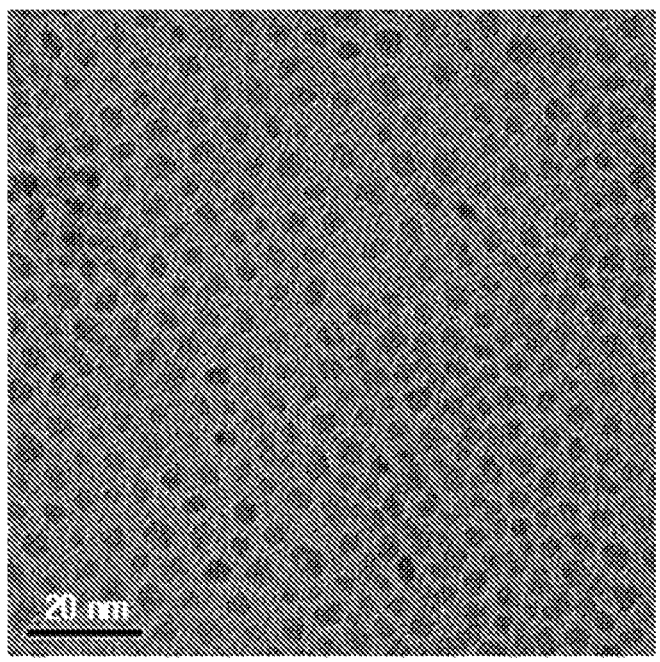

[Figure 7]
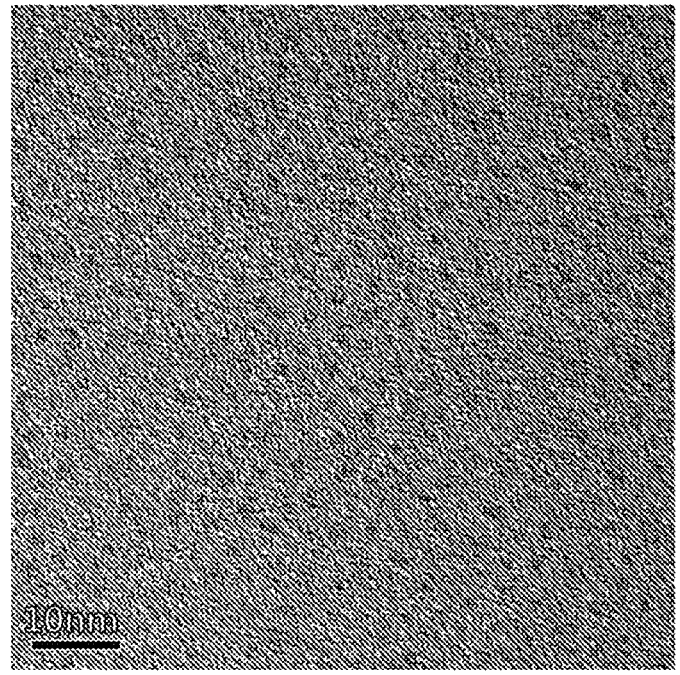
[Figure 8]
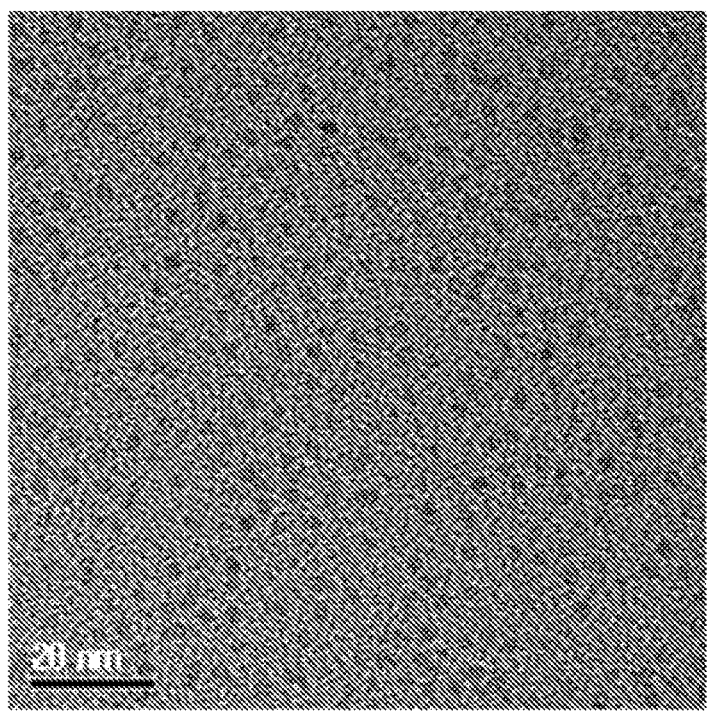

[Figure 9]
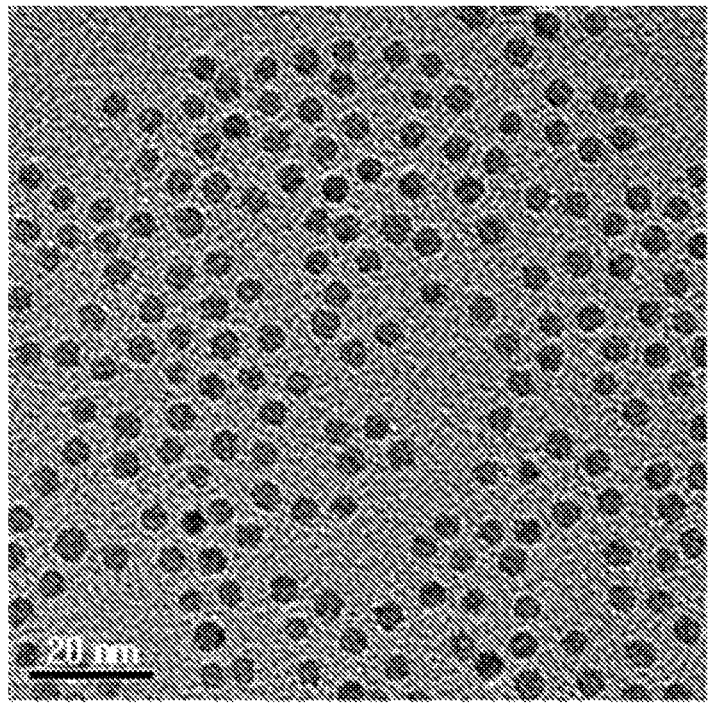
[Figure 10]
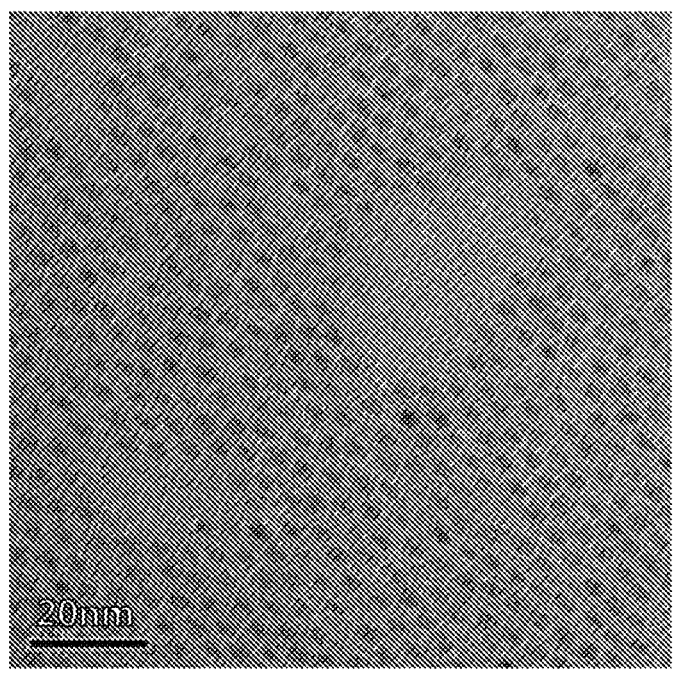

【Figure 11】
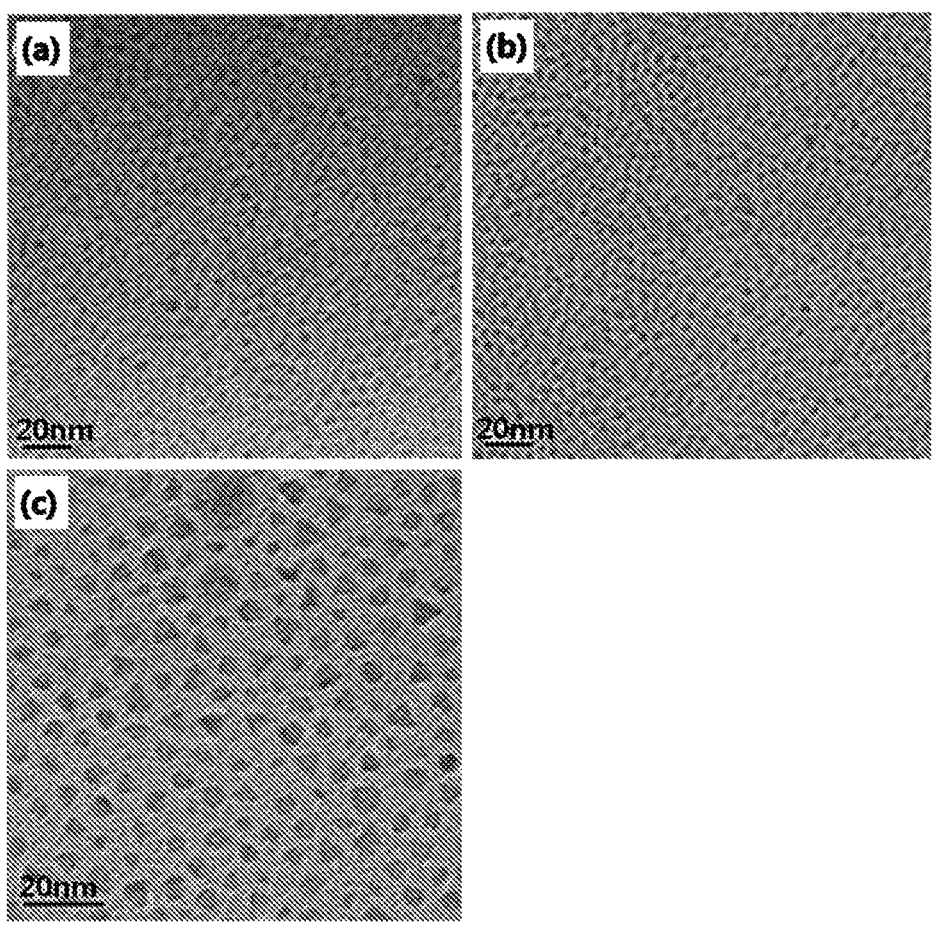

[Figure 12]
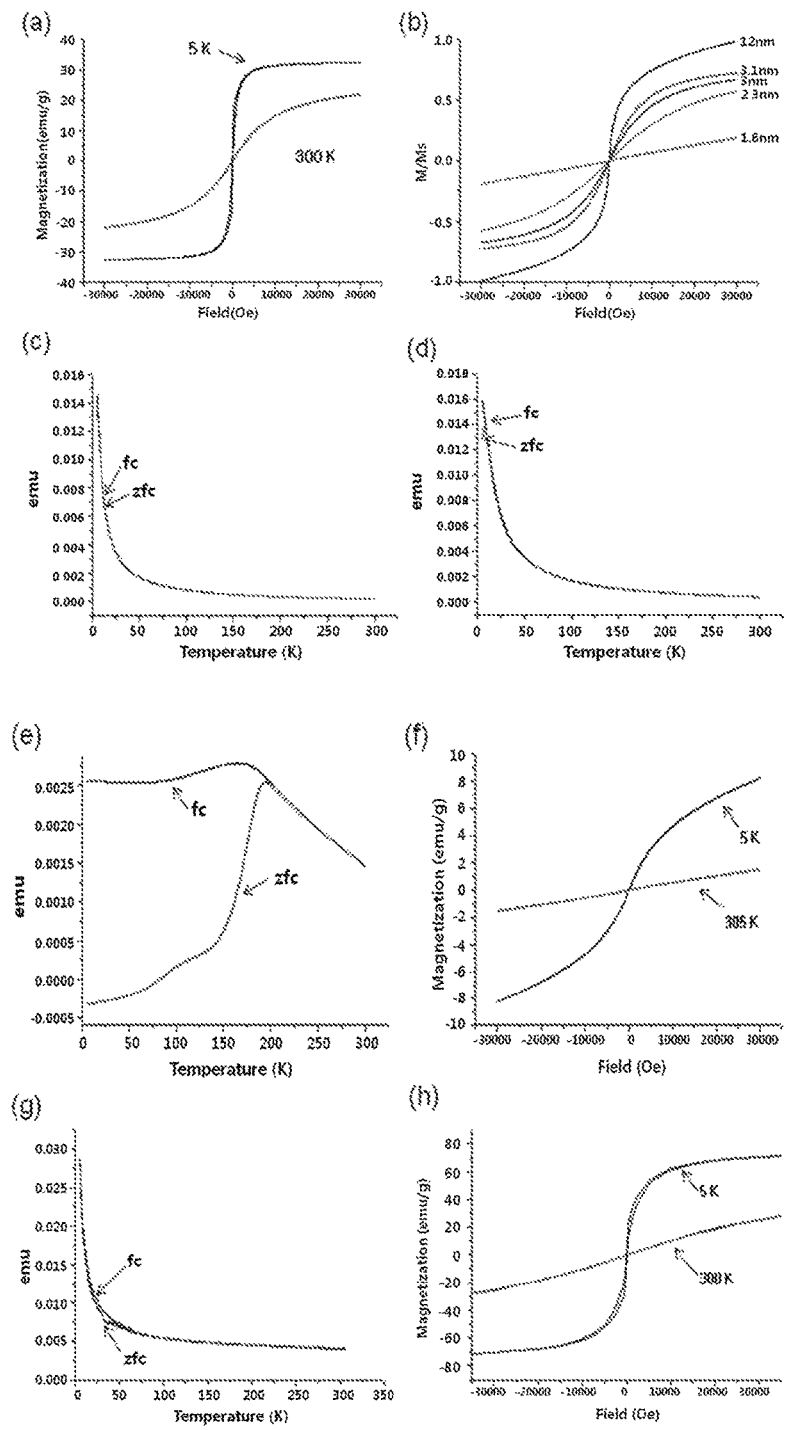

【Figure 13】
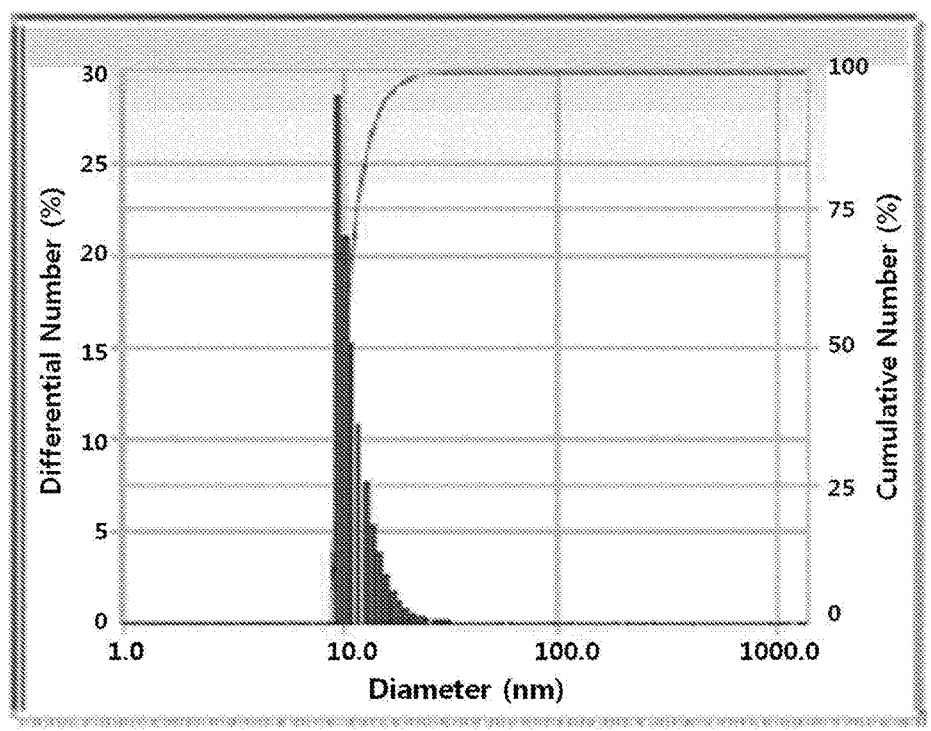

[Figure 14]
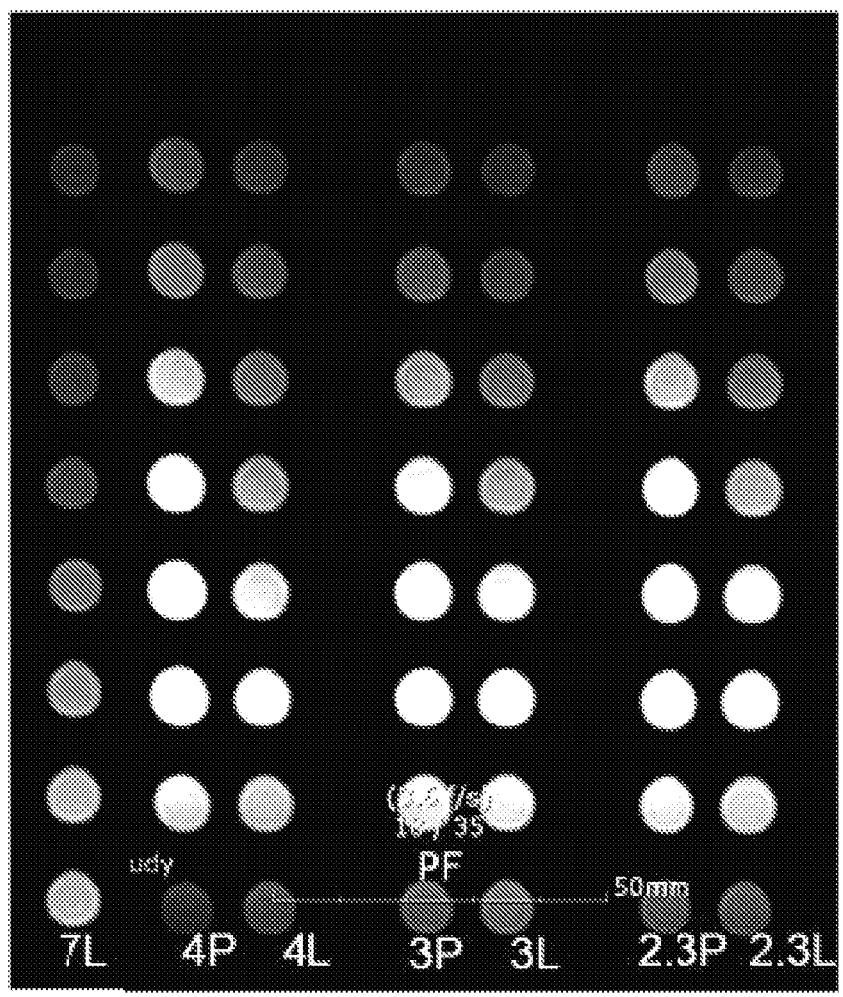

[Figure 15]
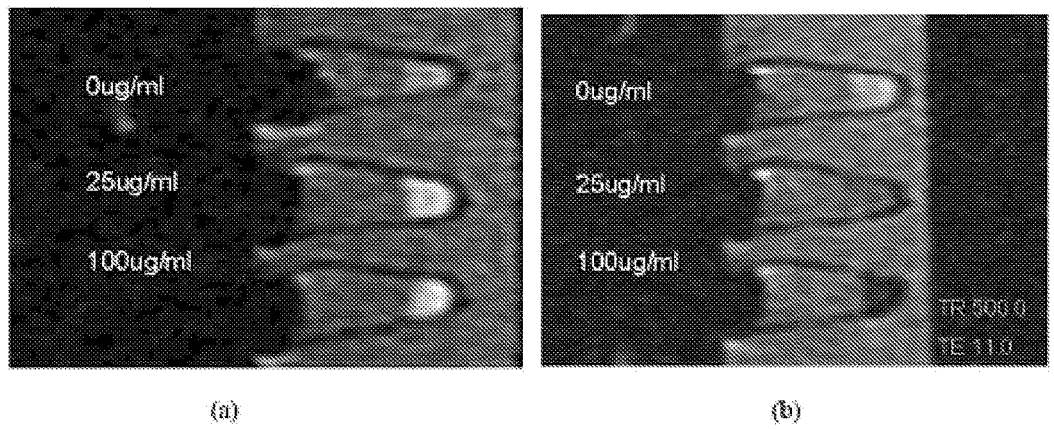
(a)           (b)

【Figure 16】
(a)
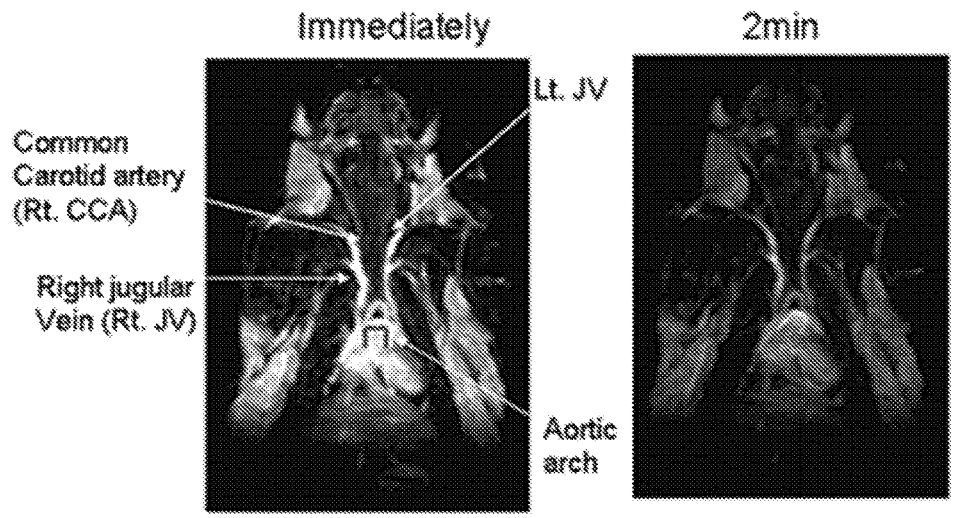
(b)
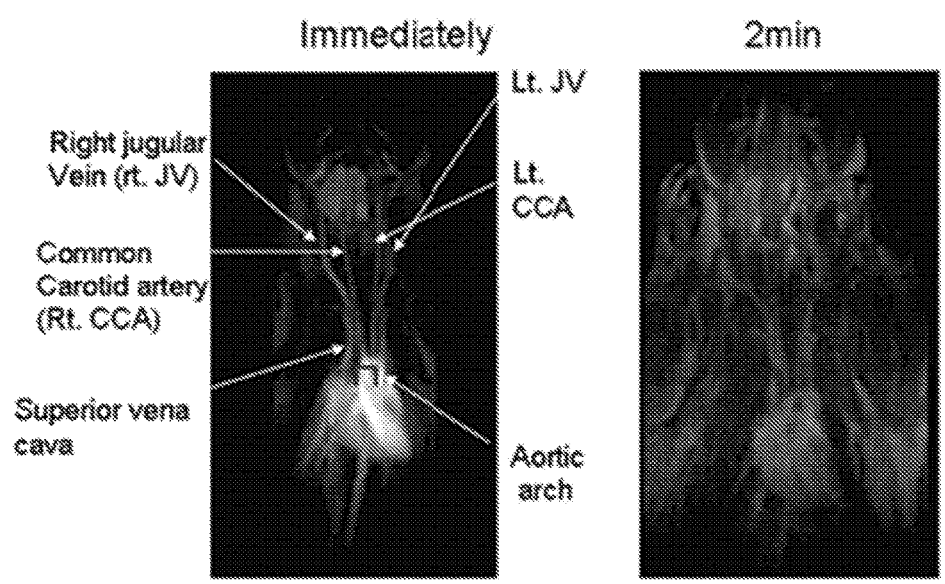

【Figure 17】
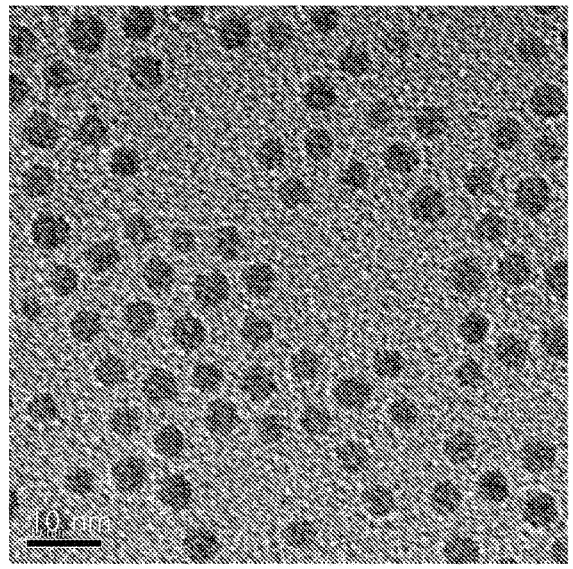
【Figure 18】
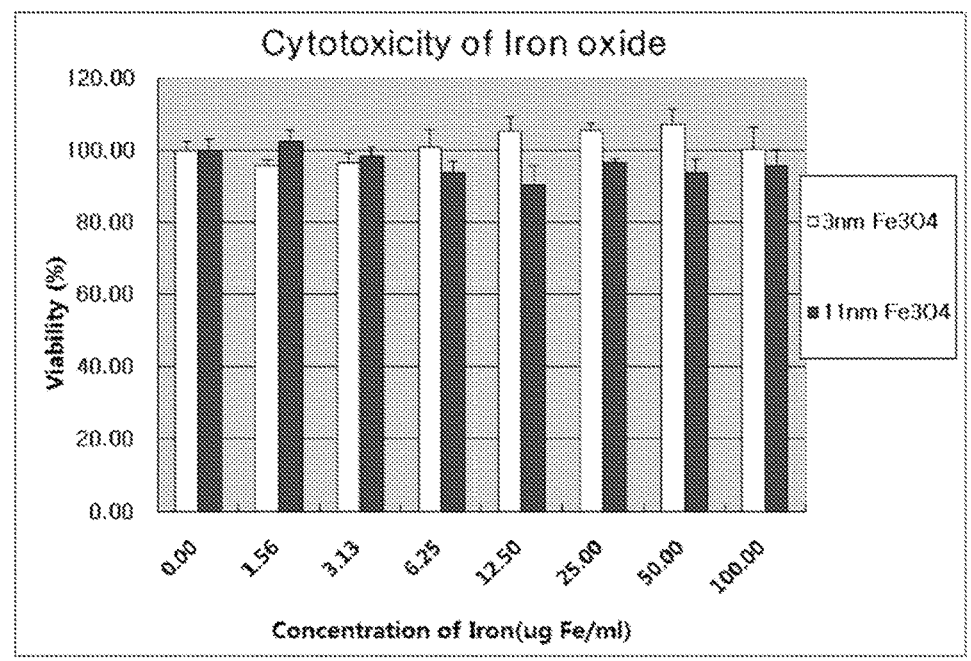

[Figure 19]
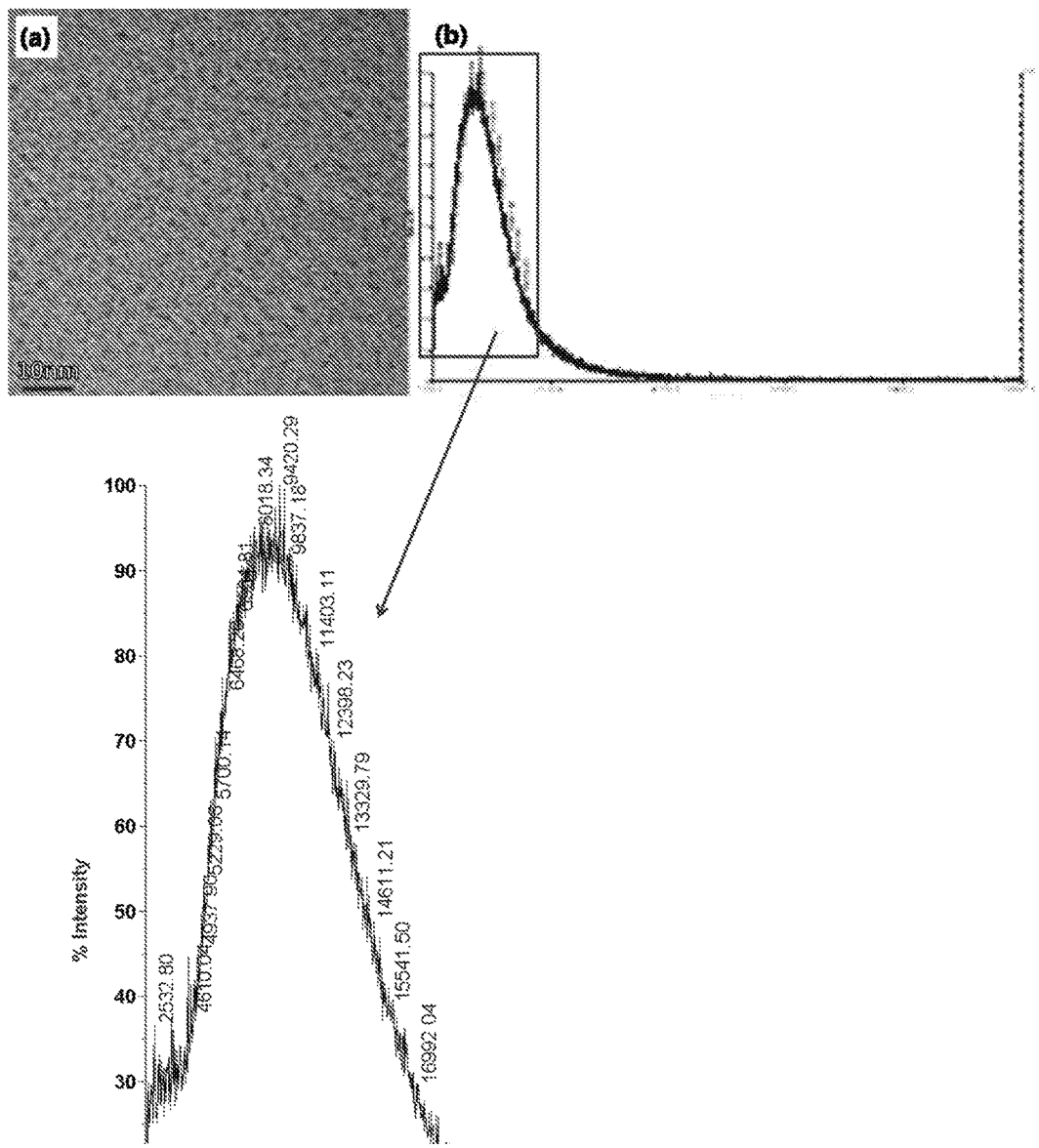

【Figure 19】Continued
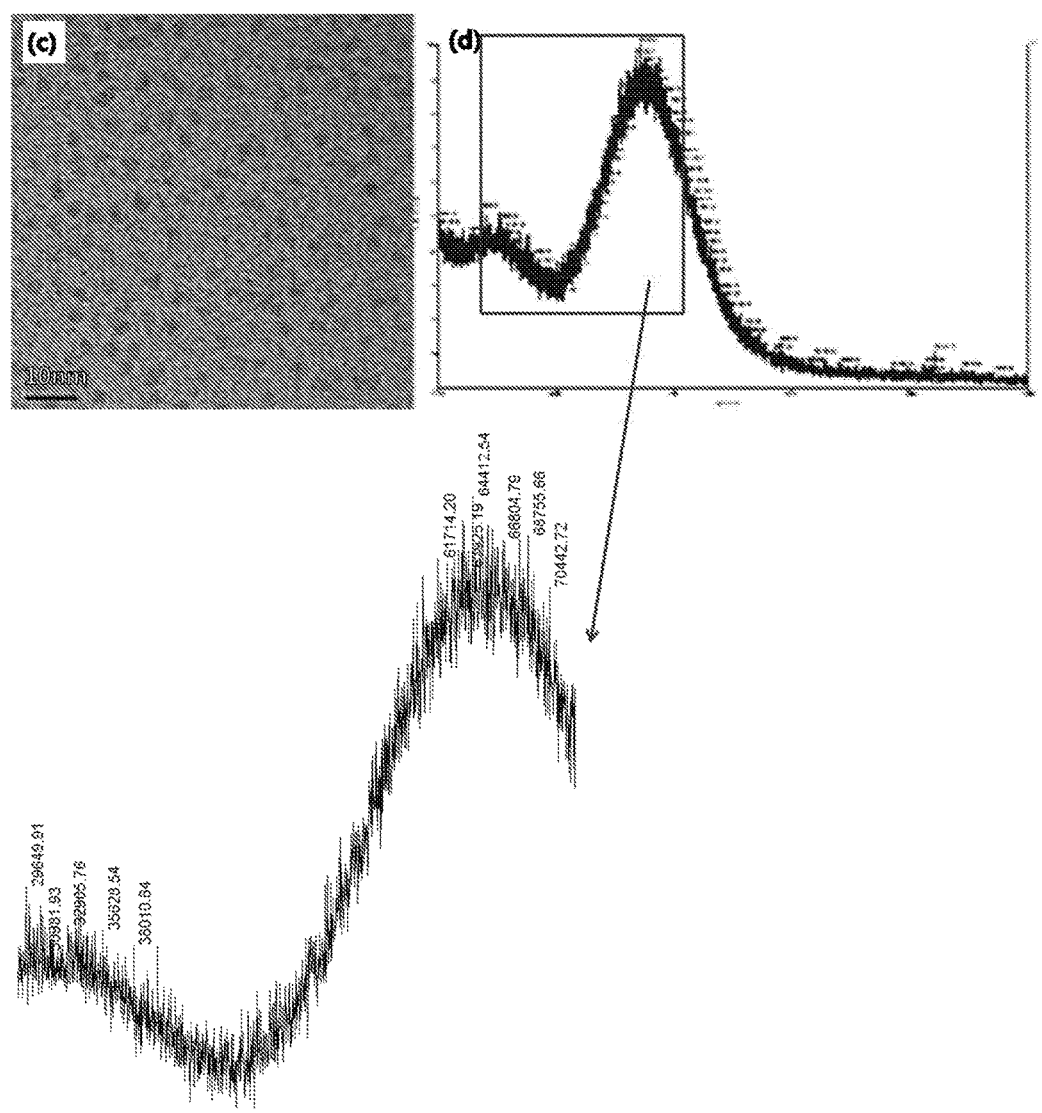

[Figure 19] Continued
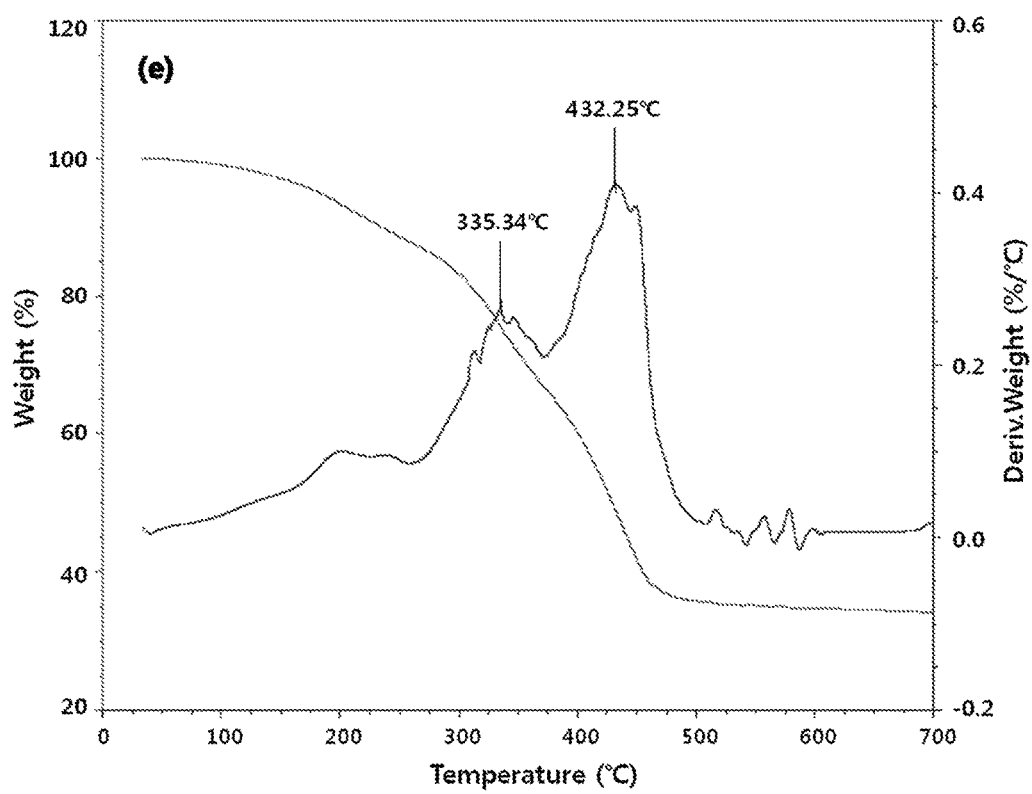

【Figure 20】
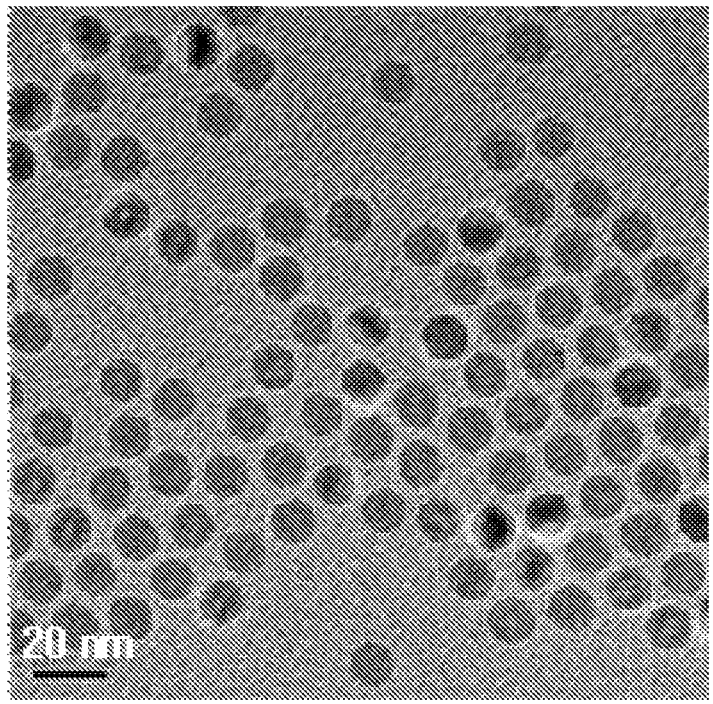
【Figure 21】
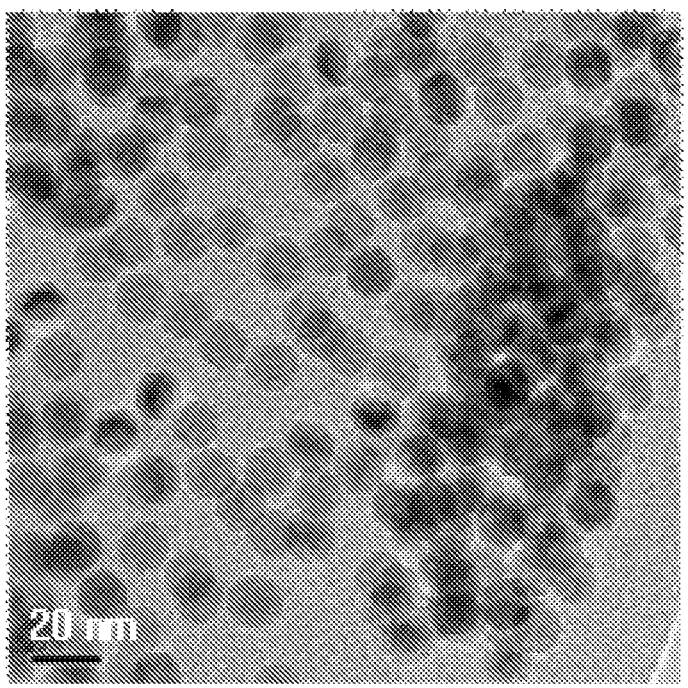

【Figure 22】
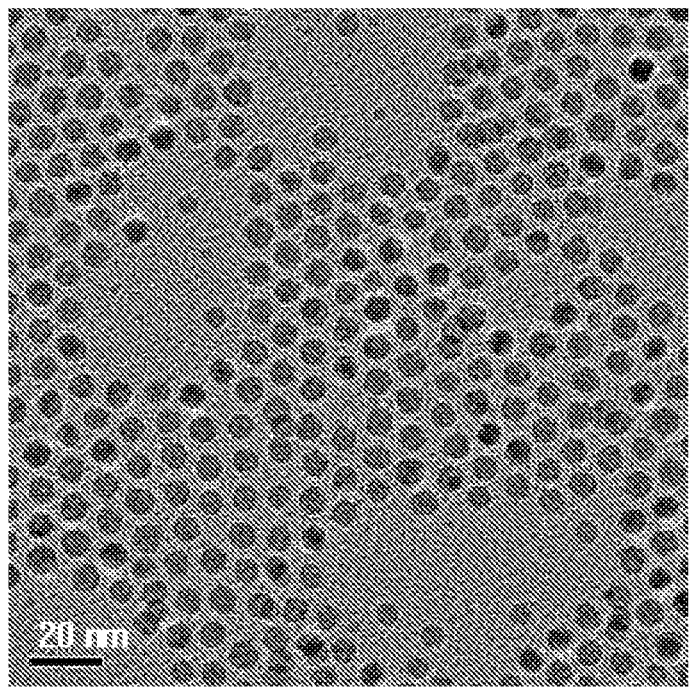
【Figure 23】
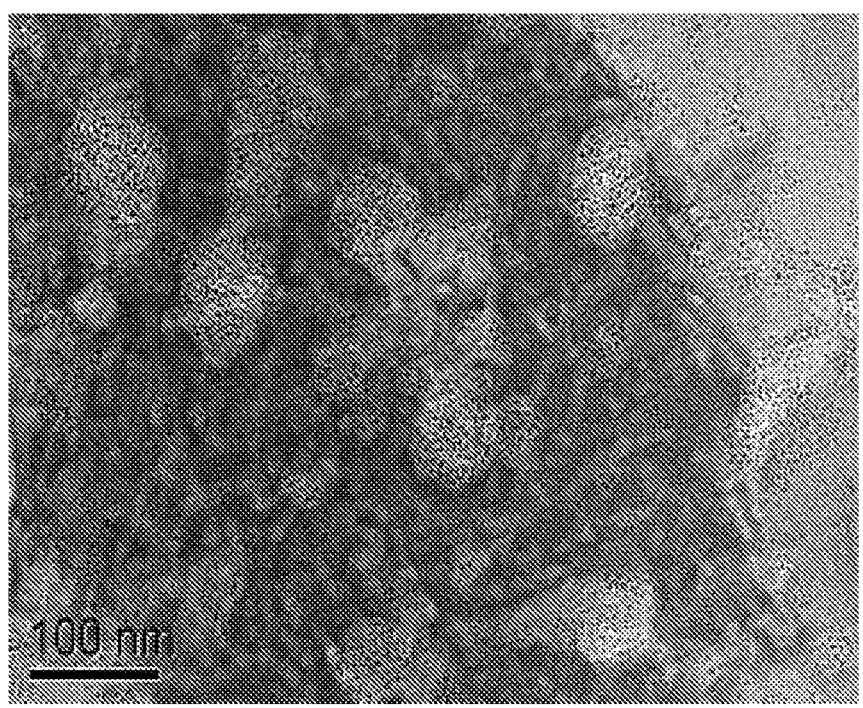

[Figure 24]
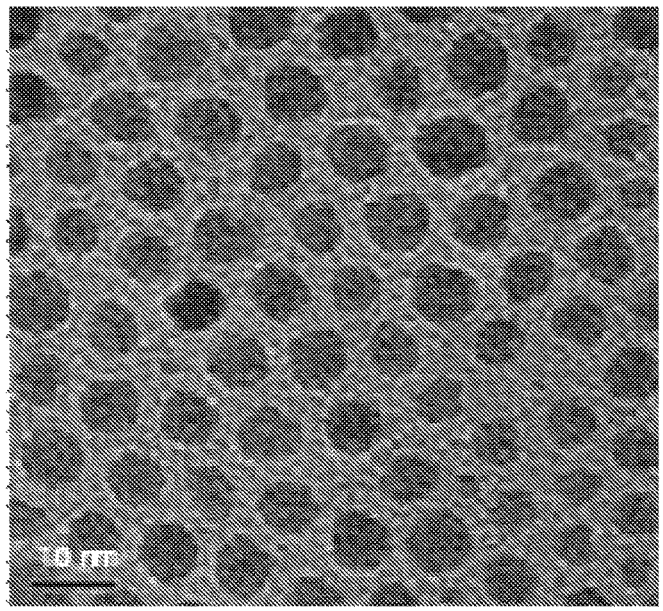
[Figure 25]
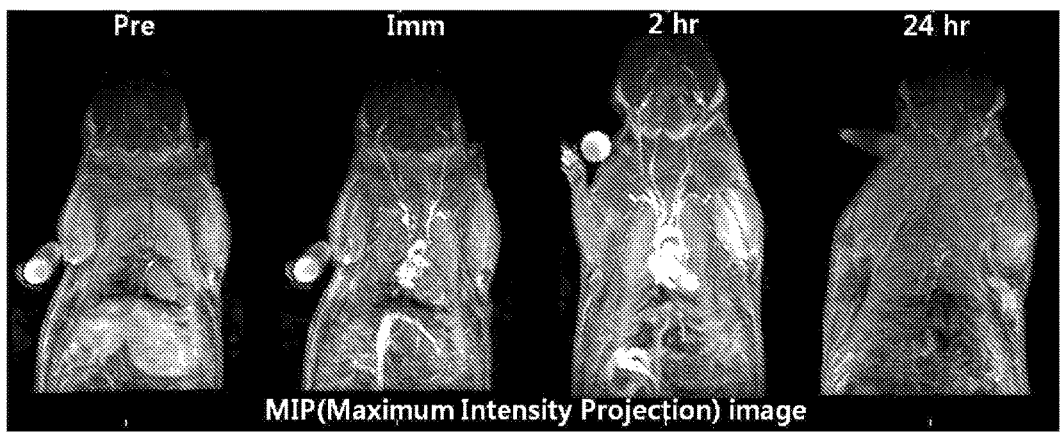

PREPARATION OF EXTREMELY SMALL AND UNIFORM SIZED, IRON OXIDE-BASED PARAMAGNETIC OR PSEUDO-PARAMAGNETIC NANOPARTICLES AND MRI T1 CONTRAST AGENTS USING THE SAME

TECHNICAL FIELD

The present invention relates to a preparation method of uniform sized iron oxide-based paramagnetic or pseudo-paramagnetic nanoparticles, iron oxide-based nanoparticles prepared by the same, and an MRI T1 contrast agent including the same. More particularly, the present invention relates to a method for preparation of iron oxide nanoparticles having a extremely small and uniform size of 4 nm or less based on thermal decomposition of iron oleate complex, iron oxide nanoparticles prepared by the same, and a T1 contrast agent including paramagnetic or pseudo-paramagnetic nanoparticles.

BACKGROUND ART

A great deal of study involving various kinds of nanoparticles has recently and actively been conducted in biomedical fields such as cell staining, cell separation, in vivo drug delivery, gene delivery, diagnosis and treatment of disease or abnormality, molecular imaging, or the like.

In order to identify substantial significance of medical applications of such nanoparticles, satisfactory results should be achieved both in-vitro and in-vivo.

That is, nanoparticles with beneficial effects primarily proved through cell experiments, are then subjected to secondary animal testings to support that the tested nanoparticles so they may be applicable for medical use.

Magnetic resonance imaging (MRI) is a well known method for provision of anatomic, physiological and/or biochemical information of a human body through images by spin relaxation of hydrogen atoms in a magnetic field and is at present an excellent image diagnostic instrument that enables real time imagination of organs of an animal or human in a non-invasive way.

For precious and various utilizations of MRI in biological science or medical fields, a process of injecting a foreign substance into the body to increase contrast of an (MRI) image is used. In this regard, the foreign substance is often referred to as a contrast agent. Such a contrast agent may be a substance using super-paramagnetic or paramagnetic material that induces contrast of signals on a site to be observed through MRI, thus allowing the site to be clearly distinguished.

On MRI images, contrast between tissues is a phenomenon occurred due to difference in relaxation between tissues, wherein the relaxation refers to recovery of nuclear spin of water molecules in the tissues to an equilibrium state. The contrast agent influences such relaxation and thus may increase the difference in relaxation between tissues and induce variation in MRI signals, thus enabling clearly distinguishable contrast of the tissues. However, the contrast agent may cause differences in utility and precision, depending on the characteristics and functions of the contrast agent, subjects for injection of the contrast agent, or the like.

In addition, when contrast is improved using the contrast agent which helps to regulate image signals of specific organs and/or tissues to be higher or lower than adjacent organs and/or tissues, a more distinctive (sharp) image is created. A contrast agent increasing the level of image signals at a desired site of the body, from which MRI images are obtained, than that of the other site (adjacent to the desired site), may be referred to as a 'positive' contrast agent ('T1 contrast agent'). On the other hand, a contrast agent decreasing the level of image signals at a desired site than that of the other side may be referred to as a 'negative' contrast agent ('T2 contrast agent'). More particularly, the MRI contrast agent may be classified into a T1 contrast agent using high spin of a paramagnetic material and a T2 contrast agent using magnetic inhomogeneity around a paramagnetic or super-paramagnetic material. The 'positive' contrast agent relates to T1 relaxation, that is, longitudinal relaxation. Such longitudinal relaxation means that, after a magnetized component 'Mz' in Z-axis direction of the spin absorbs RF energy impact applied from X-axis, the magnetized component is aligned along Y-axis on an X-Y plane and emits energy to the outside, in turn returning to the original value (or state) of Mz. The foregoing action is expressed as 'T1 relaxation.' The time taken for returning Mz to 63% of an original value refers to "T1 relaxation time' and, as the T1 relaxation time is decreased, MRI signals are greater, which in turn, decreases a period of time for acquiring images.

Likewise, the 'negative' contrast agent relates to T2 relaxation, that is, transversal relaxation. As described above, after the magnetized component 'Mz' in Z-axis direction of the spin absorbs RF energy impact applied from X-axis, the magnetized component is aligned along Y-axis on an X-Y plane and spontaneously decays and/or emits energy to adjacent spins, in turn returning to the original value of Mz. In this regard, another spin component 'My' equally widen on the X-Y plane is decayed by an exponential function and this is expressed as 'T2 relaxation.' A time taken until My is decayed to 37% of an original value refers to 'T2 relaxation time' and a My value measured through a receiving coil mounted on Y-axis by a function of time, wherein the My value is decreased over time, refers to a free induction decay (FID). Tissues with a short T2 relaxation time are shown as a dark region on the MRI.

In MRI contrast agents commercially available on the market, paramagnetic compounds are used as a 'positive' contrast agent while super-paramagnetic nanoparticles are used as a 'negative' contrast agent.

A current T2 contrast agent includes iron oxide nanoparticles such as SPIO (superparamagnetic iron oxide). In this case, T2 contrast is a negative contrast, that is, a negative contrast method wherein desired sites are darker than the surrounding part. Therefore, this method does not embody remarkable contrast effects and has a demerit of causing blooming effect to contrast a larger area than an actual size.

On the other hand, the T1 contrast agent has a merit of offering positive contrast to brightly display a desired site, and comprises a high spin material. Therefore, a gadolinium complex having 7 hole-spins in 4f orbital is usually employed. However, the gadolinium complex has very short in vivo and/or vascular retention time due to a relatively small molecular weight, causing difficulties in precisely diagnosing. Further, the above T1 contrast agent cannot be used to persons having weak kidneys because of a danger to derive nephrogenic systemic fibrosis and has recently received the warning by the U.S. Food and Drug Administration. Accordingly, there is a strong need for development of an improved T1 contrast agent that may solve such disadvantages of the gadolinium complex including, for example, short retention time, severe toxicity to patients with kidney diseases, or the like.

Among new trends in research on T1 contrast agents, an article regarding the use of manganese oxide nanoparticles having 5 hole-spins at 3d orbital has been disclosed (H. B. Na et al., Angew. Chem. Int. Ed. 2007, 46, 5397).

A manganese oxide nanoparticle has advantages such as a high T1 relaxation effect, which is a characteristic of manganese ions, and easy bonding to target molecules and easy intracellular injection which are characteristics of the nanoparticle. However, in the case where the manganese oxide nanoparticle is introduced into endosome, manganese ions escape from the nanoparticle due to internal acidic environments. Therefore, if such manganese ions remain in the body, these may cause a calcium channel disturbance problem (L. K. Limbach, et al., Environ. Sci. Technol. 2007, 41, 4158).

In order to overcome the above disadvantages, use of iron oxide as a T1 contrast agent, wherein the iron oxide has five hole-spins as well as higher biocompatibility than manganese, may be proposed.

General iron oxide (especially, magnetite or maghemite) nanoparticles are super-paramagnetic near room temperature. Due to such super-paramagnetic properties, that is, high magnetization, a T2 level is increased and susceptibility characteristics may occur, thus causing problems such as signal distortion. Consequently, it has been reported that magnetite is not suitable to be used as a T1 contrast agent (Y.-w. Jun, et al. J. Am. Chem. Soc. 2005, 127, 5732).

However, the foregoing problems may be overcome by controlling the size of iron oxide nanoparticles. More particularly, as the size of iron oxide particles is decreased, magnetic properties thereof may be reduced, which in turn deteriorates magnetic inhomogeneity. Accordingly, use of the iron oxide nanoparticles as a T1 contrast agent may be expected. For instance, U.S. Pat. No. 6,638,494 (inventor: Herbert Pilgrim) disclosed enhancement of T1 relaxivity (r1) by decreasing a particle size of super-paramagnetic iron oxide. According to the patent, iron oxide nanoparticles synthesized by co-precipitation, which have a particle size of 1 to 10 nm, and an average size (d50: median) of 2 to 4 nm, and hydrophilic surface, show that T1 relaxivity ranges from 2 to 50 L/mmol·sec and r2/r1 is 5 or less. However, although the particle average size (median) is small, a range of the particle size is considerably broad such as 1 to 10 nm, to thereby produce irregularity in particle size. If the size of an iron oxide particle is 4 nm or greater, the T2 effects may increase rapidly with the particle size. Therefore, even though the average size is small, improvement in T1 relaxivity is not so high when the particles have irregular size. Therefore, these nanoparticles are also not suitable to be used as a T1 contrast agent.

Among recent studies, use of iron oxide nanoparticles with a size of 4 to 6 nm as a T1 contrast agent has been reported (E. Taboada et al., Langmuir, 2007, 23, 4583; U. I. Tromsdorf et al., Nano Lett. 2009, 9, 4434). However, due to a relatively large particle size, T2 effects are still significant, thus the nanoparticles entail limitations in application thereof as a TI contrast agent.

Combidex® (AMAG Co.) which is currently under clinical trials in regard to use thereof as a T2 contrast agent for lymph nodes, had also been investigated for T1 contrast performance thereof. However, since an average size of iron oxide nanoparticles was relatively large in the range of 4 to 6 nm and a size of constitutional particles is irregular, it was known that T2 effect is predominant over T1 effect (Claire Corot et al., Advanced Drug Delivery Reviews 58 (2006) 1471).

Further, there is a method for preparation of iron oxide particles having a uniform size through thermal decomposition. However, strict requirements for the preparation of iron oxide nanoparticles having a size of 4 nm or less are needed, in turn not being preferable in commercial applications (Jongnam Park, et al., Nature Mater., 3(2004), 891).

Moreover, even if nanoparticles having a size of 4 nm or less may be prepared, raw materials are expensive and/or have severe toxic properties, thus having little significance in the aspect of commercial applications (Xiaowei Teng, J. Mater. Chem., 14(2004), 774).

Accordingly, synthesis and mass-production of iron oxide nanoparticles having a extremely small and uniform size of 4 nm or less, in a highly reproducible manner at low costs, as well as T1 contrast research using the same, have not yet been reported, which are still required.

DISCLOSURE

Technical Problem

As an existing magnetic resonance T1 contrast agent, a gadolinium complex has a considerably small molecular weight, thus showing a too short in vivo and vascular retention time. In addition, the complex may cause severe toxicity problems to patients with kidney diseases. Since an iron oxide nanoparticle is a crystal, it has a relatively particle size, to thereby lead to extend the in vivo and vascular retention time, and it still has minimal toxicity. Based on such advantages, it is intended to develop a new T1 constant agent using the iron oxide nanoparticles. However, iron oxide nanoparticles prepared by conventional methods are so large that they still entails a problem of highly predominant T2 effect over T1 effect and, therefore, may not be suitably used for T1 contrast.

Accordingly, an object of the present invention is to provide a method for manufacturing iron oxide nanoparticles, wherein the nanoparticles are able to be used as a T1 contrast agent, have an extremely small and uniform particle size, are easily produced, and enable mass production thereof.

More particularly, the foregoing object relates to provision of a method for preparation of iron oxide nanoparticles, wherein the nanoparticles have paramagnetic or pseudo-paramagnetic (hereinafter, referred to as '(pseudo)paramagnetic') properties, size uniformity (average size±1 nm) and a small average size of 4 nm or less, as compared to conventional iron oxide nanoparticles with super-paramagnetic properties.

Another object of the present invention is to provide iron oxide nanoparticles which have (pseudo)paramagnetic properties, size uniformity (average size±1 nm) and a extremely small average size of 4 nm or less, and which have not been made in the related art.

Another object of the present invention is to provide an MRI T1 contrast agent including (pseudo)paramagnetic iron oxide nanoparticles described above and, more particularly, an MRI T1 contrast agent including iron oxide nanoparticles, with various advantages, wherein: the contrast agent has improved T1 contrast effects without image distortion while providing bright images; is present in the nanoparticle form to increase intracellular penetration rate and intracellular uptake capacity; imparts target-specific contrast effects; is easily delivered to a target and safely eliminated from the body; minimizes side effects, or the like. Moreover, the present invention provides a T1 contrast agent having desired in vivo and vascular retention time, which is not too short (that is, relatively extended), as compared to conventional Gd-based T1 contrast agents.

Technical Solution

In order to overcome the foregoing problems in the related art, the present inventors have implemented intensive and extensive studies and accomplished synthesis of iron oxide nanoparticles having extremely small and uniform size of 4 nm or less based on thermal decomposition of iron oleate complex through a simple process. Using the synthesized iron oxide nanoparticles as a T1 contrast agent, the present invention has been completed.

Accordingly, the present invention provides a method for preparation of iron oxide nanoparticles, which includes (a) reacting: an iron complex having iron as a central atom and a carboxylate group having 4 to 25 carbon atoms ('C4 to C25 carboxylate group') that is bonded to the central atom in a ligand form; a C4 to C25 fatty acid: and a C4 to C25 aliphatic alcohol or C4 to C25 aliphatic amine at 150 to 350° C. to prepare the iron oxide nanoparticles and, after operation (a), further includes (b) dispersing a precipitate in an organic solvent, wherein the precipitate is obtained by cooling and washing the nanoparticles described above.

The iron oxide nanoparticles prepared as above may have a size of 4 nm or less and (pseudo)parametric properties, thus being usable as an MRI T1 contrast agent.

An iron precursor used in the preparation of iron oxide nanoparticles may comprise an iron atom and a C10 to C22 fatty acid group in a ligand form that is bonded to the iron atom and, more preferably, is an iron oleate complex (hereinafter, 'iron oleate').

In addition, the fatty acid and/or aliphatic alcohol (or aliphatic amine) used in the preparation of iron oxide nanoparticles may include C10 to C22 fatty acids and/or aliphatic alcohols (or aliphatic amines). More preferably, the fatty acid and aliphatic alcohol are oleic acid and oleyl alcohol while the aliphatic amine is oleyl amine.

Meanwhile, with regard to practical processing conditions, the preparation of iron oxide nanoparticles described above may be performed by heating reaction materials, that is, an iron complex, fatty acid and aliphatic alcohol (or aliphatic amine), in a mixed state, from room temperature to 200 to 310° C. at a temperature elevation rate of 5° C./min or more, and allowing reaction at 200 to 310° C. for 5 to 60 minutes.

According to another object, the present invention also provides iron oxide nanoparticles prepared according to the foregoing extremely small and uniform sized preparation method. In this regard, each of the iron oxide nanoparticles may have a size of 4 nm or less and exhibit (pseudo) paramagnetic properties. The size of the iron oxide nanoparticle prepared according to the present invention may be controlled by regulating molar ratios of the reaction materials such as C4 to C25 fatty acid, C4 to C25 aliphatic alcohol (or aliphatic amine) introduced during the preparation.

Since the iron oxide nanoparticles have organic materials capped on their surface, which come from reaction materials, they are hydrophobic and well dispersible in nonpolar organic solvent such as hexane, toluene, and the like.

Further, the present invention provides hydrophilic iron oxide nanoparticles by modifying the surface of the hydrophobic nanoparticles with hydrophilic materials through ligand exchanging or encapsulating methods.

The hydrophilic iron oxide nanoparticles, according to the present invention, may be obtained by modifying the surface of iron oxide with polyethyleneglycol ('PEG'), phospholipid-PEG, PEG-phosphate, monosaccharide phosphate, derivatives of monosaccharide phosphates, betaines or citric acid. More preferably, the surface of iron oxide may be modified with a PEG-phosphate (PO-PEG) molecule that has a PEG bonded to a phosphate group or phosphine oxide group, glucose 6-phosphate, glucose 6-phosphate-ethanolamine, glucose 6-phosphate-PEG, Betaine or citric acid.

Further, the present invention provides colloidal solution including the hydrophilic iron oxide nanoparticles dispersing the nanoparticles in water.

Further, the present invention provides magnetic resonance imaging T1 contrast agent including the colloidal solution of hydrophilic iron oxide nanoparticles.

According to the present invention, even where the iron oxide nanoparticle is the one synthesized by any known method, the nanoparticle may be (pseudo)paramagnetic if it has a size of 4 nm or less and, therefore, nanoparticles may exhibit improved T1 contrast effects.

An alternative method for preparation of iron oxide nanoparticles according to the present invention may include reacting: an iron complex having iron as a central atom and a C4 to C25 carboxylate group that is bonded to the central atom in a ligand form; and a C4 to C25 fatty acid at 290 to 310° C. with a temperature elevation rate of 3 to 3.5° C./min to prepare the iron oxide nanoparticles. Another alternative method for preparation of iron oxide nanoparticles according to the present invention may include primarily reacting: an iron complex having iron as a central atom and a C4 to C25 carboxylate group that is bonded to the central atom in a ligand form; and a C4 to C25 fatty acid at 265 to 275° C., followed by conducting a secondary reaction thereof at 315 to 325° C., to prepare the iron oxide nanoparticles.

The present invention is not particularly limited to the foregoing objects and, instead, the other objects and advantages of the present invention will be apparent from the following detailed description and clearly understood by preferred embodiments of the present invention.

Moreover, it will be easily understood that other purposes, features and aspects of the present invention may be realized by measures and/or means and combinations thereof described by the appended claims.

Advantageous Effects

According to the present invention, (pseudo)paramagnetic iron oxide nanoparticles having an extremely small and uniform size of 4 nm or less may be reproducibly and massively manufactured using raw materials at low costs by an easier and simple preparation process, compared to existing methods in the related art. Also, a size of the nanoparticles may be easily controlled.

In addition, iron oxide nanoparticles manufactured according to the foregoing method have a uniform size distribution, compared to the existing methods in the related art, thereby imparting constant T1 contrast effects.

Furthermore, the present invention provides a T1 contrast agent including (pseudo)paramagnetic iron oxide nanoparticles, to thereby enable high quality of T1 contrast, which could not be given by the existing methods in the related art.

DESCRIPTION OF DRAWINGS

The above and other objects, features and advantages of the present invention will become apparent from the following description of preferred embodiments given in conjunction with the accompanying drawings, in which:

FIG. 1 shows transmission electron microscopy (TEM) images of 3 nm-size iron oxide nanoparticle synthesized by a method described in Example 1, more particularly; (a) a TEM image; (b) a TEM image in a wide range; (c) a high resolution-transmission electron microscopy (HR-TEM) image; and (d) a selected area electron diffraction (SAED) pattern;

FIG. 2 shows a X-ray diffraction (XRD) spectrum of 3 nm-size nanoparticles synthesized by a method described in Example 1;

FIG. 3 shows a TEM image of 2.3 nm-size iron oxide nanoparticles synthesized by a method described in Example 2;

FIG. 4 shows a TEM image of 1.8 nm-size iron oxide nanoparticles synthesized by a method described in Example 3;

FIG. 5 shows a TEM image of 3.3 nm-size iron oxide nanoparticles synthesized by a method described in Example 4;

FIG. 6 shows a TEM image of 3.5 nm-size iron oxide nanoparticles synthesized by a method described in Example 5;

FIG. 7 shows a TEM image of 1.6 nm-size iron oxide nanoparticles synthesized by a method described in Example 6;

FIG. 8 shows a TEM image of 2.4 nm-size iron oxide nanoparticles synthesized by a method described in Example 7;

FIG. 9 shows a TEM image of 3.5 nm-size iron oxide nanoparticles synthesized by a method described in Example 8;

FIG. 10 shows a TEM image of 2.3 nm-size iron oxide nanoparticles synthesized by a method described in Example 9;

FIG. 11 of (a) shows a TEM image of 2.7 nm-size iron oxide nanoparticles synthesized by a method described in Example 10; (b) shows a TEM image of iron oxide nanoparticles synthesized by a method described in Comparative Example 1; and (c) shows a TEM image of iron oxide nanoparticles synthesized by a method described in Comparative Example 2;

FIG. 12 of (a) shows M-H graphs at 5K and 300K, respectively, of 3 nm-size nanoparticles synthesized by the method described in Example 1; (b) shows variation in M-H graph at 300K of nanoparticles with particle size; (c) shows zero field cooling and field cooling M-T graphs of 2.3 nm-size nanoparticles synthesized by the method described in Example 2, respectively; (d) shows an M-T graph of 3 nm-size nanoparticles synthesized by a method described in Example 1; (e) shows an M-T graph of 12 nm-size nanoparticles synthesized by a method described in Comparative Example 3; (f) shows M-H graphs at 5K and 300K, respectively, of 1.6 nm-size nanoparticles synthesized by the method described in Example 6; (g) shows an M-T graph of the nanoparticle in Example 6; and (h) shows M-H graphs at 5K and 300K, respectively, of 2.3 nm-size nanoparticles synthesized by the method described in Example 9;

FIG. 13 illustrates a distribution of number-average hydrodynamic diameters (number-average of 11.8 nm) of 3 nm-size nanoparticles which are dispersed in water by using PEG-phosphate (PO-PEG) according to a method described in Example 13;

FIG. 14 shows MRI phantom T1 image of dispersions which are prepared by primarily modifying the surface of iron oxide nanoparticles with PEG-phosphate (PO-PEG) and phospholipid PEG, respectively, with particle size, and then secondarily dispersing the surface-modified nanoparticles in water; in particular, in the case where PO-PEG is used to treat the nanoparticles having a size of 2.3 nm, 3 nm, 4 nm and 7 nm, respectively, they are each indicated as 2.3 P, 3 P and 4 P; likewise, in the case where phospholipid-PEG is used to treat the foregoing nanoparticles, they are each indicated as 2.3 L, 3 L, 4 L and 7 L;

FIG. 15 shows cell phantom MRI results of 3 nm-size nanoparticles and 12 nm-size nanoparticles, respectively; in particular, (a) shows cell phantom MR image of 3 nm-size nanoparticles; and (b) shows cell phantom MR image of 12 nm-size nanoparticles;

FIG. 16 shows clear contrast images of jugular veins, carotid arteries and aortic arch, which are obtained using the inventive nanoparticles, as compared to a gadolinium complex, Gadovist® (Bayer Schering Co.) (a) shows in vivo MRI vascular contrast image using 3 nm-size nanoparticles; and (b) shows in vivo MRI vascular contrast image using Gadovist®;

FIG. 17 shows a TEM image of 4 nm-size iron oxide nanoparticles synthesized by a method described in Example 20;

FIG. 18 illustrates MTT assay results of MCF-7 cells using hydrophilic-modified iron oxide nanoparticles according to Example 21;

FIG. 19 illustrates molecular weight assay results of iron oxide nanoparticles by means of MALDI-TOF in Example 22;

FIG. 20 shows a TEM image of 12 nm-size iron oxide nanoparticles synthesized by a method described in Comparative Example 3;

FIG. 21 shows a TEM image of 12 nm-size iron oxide nanoparticles synthesized by a method described in Comparative Example 4;

FIG. 22 shows a TEM image of 7 nm-size iron oxide nanoparticles synthesized by a method described in Comparative Example 5;

FIG. 23 shows a TEM image of 4 nm-size iron oxide nanoparticles, which were encapsulated in an aggregate form, followed by negative staining, according to the method described in Comparative Example 6; and FIG. 24 shows a TEM image of 6 nm-size iron oxide nanoparticles synthesized by comparative Example 7.

FIG. 25 shows an enhanced MRI vascular contrast images using the 3 nm-size nanoparticles capped by glucose 6-phosphate described in example 17.

BEST MODE

The foregoing objects, features and advantages will become more apparent from the following description of preferred embodiments of the present invention with reference to accompanying drawings, which are set forth hereinafter. Accordingly, those having ordinary knowledge in the related art to which the present invention pertains will easily embody technical ideas or spirit of the present invention. In addition, the terminology used herein includes the meanings commonly understood in the related art by those having ordinary knowledge in the related art, except where otherwise noted. When technical configurations known in the related art are considered to make the contents obscure in the present invention, the detailed description thereof will be omitted.

Hereinafter, preferred embodiments of the present invention will be described in detail with reference the accompanying drawings.

A method for preparation of iron oxide nanoparticles according to the present invention comprises, (a) reacting:

an iron complex having iron as a central atom and a carboxylate group having 4 to 25 carbon atoms ('C4 to C25 carboxylate group,' hereinafter the same defined as above) that is bonded to the central atom in a ligand form; a C4 to C25 fatty acid; and a C4 to C25 aliphatic alcohol or C4 to C25 aliphatic amine at 150 to 350° C. to prepare the iron oxide nanoparticles and, after the preparation (a), further includes (b) dispersing a precipitate in an organic solvent, wherein the precipitate is obtained by cooling and washing the nanoparticles described above.

An iron precursor used in the preparation (a) of the iron oxide nanoparticles may be one having an iron atom and a C10 to C22 fatty acid group bonded thereto in a ligand form and examples of such ligands may include: stearic acid; oleic acid; linoleic acid; palmitic acid; palmitoleic acid; myristric acid; lauric acid; arakidonic acid; behenic acid, or the like. More preferably, the iron precursor used herein is iron oleate.

Fatty acid and aliphatic alcohol used in the preparation (a) of the iron oxide nanoparticles may include C10 to C22 fatty acid, C10 to C22 aliphatic alcohol and/or C10 to C20 aliphatic amine. Examples of the fatty acid may include: stearic acid; oleic acid; linoleic acid; palmitic acid; palmitoleic acid; myristric acid; lauric acid; arakidonic acid; ricinoleic acid; behenic acid, or the like. Examples of the aliphatic alcohol may include: stearyl alcohol (octadecanol); oleyl alcohol; linoleyl alcohol; hexadecanol; palmitoleyl alcohol; tetradecanol; dodecanol; arakidonyl alcohol; eicosanol; docosanol; hexadecanediol, or the like. Also, examples of the aliphatic amine may include: stearylamine (octadecylamine); oleylamine; hexadecylamine; palmitoleylamine; tetradecylamine; dodecylamine; arakidonylamine, or the like.

More preferably, the fatty acid and aliphatic alcohol used herein are oleic acid and oleyl alcohol, respectively. Likewise, the aliphatic amine used herein is oleyl amine.

With regard to practical processing conditions, the preparation of the iron oxide nanoparticles may be performed by heating reactive materials, that is, an iron complex, fatty acid and aliphatic alcohol (or aliphatic amine) in a mixed state, from room temperature to 200 to 310° C. with a temperature elevation rate of 5° C./min or more, and allowing reaction at 200 to 310° C. for 5 to 60 minutes.

The iron oxide nanoparticles prepared in the present invention may have a size of 4 nm or less. Characteristics of the iron oxide nanoparticles obtained according to the preparation method of the present invention are described below.

FIGS. 1(a) and (b) show TME images of 3 nm-size iron oxide nanoparticles. From the figures, it can be seen that the nanoparticles are extremely small and uniform. FIG. 1(b) shows a wide area of image to demonstrate that small particles are not aggregated but uniformly distributed throughout the wide area without large particles mixed therein. Compared to metal nanoparticles, an oxide with a low electron density and, therefore, extremely small oxide particles are not clearly observed by TEM. So, as shown in FIG. 1(c), a lattice structure is not clearly detected by HR-TEM owing to TEM electron-beam energy. But FIG. 1(d) illustrates peaks (311, 400) of typical magnetite or maghemite structure through an electron diffraction (ED) pattern.

FIG. 2 is an XRD spectrum of 3 nm-size nanoparticles. From the figure, it can be seen that 3 nm-size nanoparticles have a magnetite or maghemite structure, although they show relatively wide peaks (311, 400, 440) owing to a small size thereof. A clear distinction between magnetite and maghemite is very difficult because XRD patterns of these two structures are very similar. According to the calculation by Debye-Scherrer equation, the nanoparticles have a size of 3 nm, which is the same size as TEM images (FIG. 1), thereby demonstrating excellent crystallinity.

A size of the iron oxide nanoparticles prepared according to the present invention may be controlled by regulating a molar ratio of the reactive materials such as C4 to C25 fatty acid or C4 to C25 aliphatic alcohol (or aliphatic amine) introduced during the preparation.

According to the present invention, the size of the iron oxide nanoparticles may be reduced by decreasing a concentration of the iron precursor, so as to control the size of the iron oxide nanoparticles.

When an amount of the aliphatic alcohol (or aliphatic amine), as one of the reaction materials, is increased, nanoparticles having reduced size may be synthesized. However, the size control may depend on types of reaction materials and/or reaction conditions.

For instance, in the case where iron oleate is used as the iron precursor, nanoparticles having a smaller size may result by reducing a concentration of the reaction material, that is, the iron oleate. That is, 3 nm-size nanoparticles synthesized with an initial precursor concentration of 0.2M; and 2.3 nm-size nanoparticles synthesized with an initial precursor concentration of 0.1M. As a result, it can be understood that the size of iron oxide nanoparticles may be controlled by the amount of iron precursor.

With regard to size control based on the ratio between aliphatic alcohol (or aliphatic amine) and fatty acid, the foregoing ratio is not deemed to significantly influence variation in the size of nanoparticles. However, the size of nanoparticles is reduced by increasing an amount of the aliphatic alcohol such as oleyl alcohol.

Even when the aliphatic alcohol used herein is replaced by aliphatic amine as a weak reductive agent, iron oxide nanoparticles may be prepared. The aliphatic amine used herein may be C4 to C25 aliphatic amine and, preferably, oleyl amine.

Even when using alkanediol instead of the aliphatic alcohol, iron oxide nanoparticles may be prepared. However, in this case, iron oxide nanoparticles having a size of 4 nm or less cannot be produced.

Considering size and uniformity of iron oxide nanoparticles, temperature elevation may be relatively rapid. A temperature elevation rate may be 5° C./min or higher and, more preferably, 10° C./min or higher.

The reason of the foregoing fact may be presumed that burst nucleation suitably occurs when the temperature is rapidly raised, and such reaction is advantageous for synthesis of iron oxide nanoparticles having an extremely small and uniform size. As described above, the size and uniformity of the iron oxide nanoparticles may be controlled by regulating the temperature elevation rate. More particularly, smaller and more uniform iron oxide nanoparticles may be prepared by increasing the temperature elevation rate. In this regard, the temperature elevation rate may be 200° C./min or less.

For example, with regard to correlation between the size of iron oxide nanoparticles and the temperature elevation rate where oleic acid and oleyl alcohol are used, with the temperature elevation rates of 3.3° C./min, 5° C./min, non-uniform size particles including relatively large nanoparticles with a size of about 4 nm to 6 nm are synthesized. On the other hand, with the temperature elevation rates of 10° C./min and 20° C./min, uniform particles having a size of 3 nm and 2.7 nm are synthesized, respectively.

The iron oxide nanoparticles prepared according to the present invention become (pseudo)paramagnetic due to a reduced size thereof, to thus minimize interference with T1 relaxation caused by an increase in T2 relaxation, which in turn, is suitable to be used as an MRI T1 contrast agent. Consequently, the iron oxide nanoparticles of the present invention may be applicable to MRI contrast agents.

The iron oxide nanoparticles prepared according to the present invention are less toxic than other metal oxides, thus are biocompatible. The iron oxide nanoparticles may be used as an MRI T1 contrast agent by modifying the surface thereof with phospholipid-PEG, PEG-phosphate (PO-PEG), monosaccharide phosphates, derivatives of monosaccharide phosphates, betaines or citric acid. More preferentially the surface of iron oxide maybe modified with a PO-PEG, glucose 6-phosphate, glucose 6-phosphate-ethanol amine, glucose 6-phosphate-PEG or citric acid. The capping materials on the nanoparticle affect strongly the hydrodynamic size, stability in water and toxicity. Even when the iron oxide core size is extremely small, hydrophilic composition after ligand exchanging can be large enough to increase T2 effects. So the hydrophilic layer is crucial in a T1 MRI contrast agent.

With regard to preparation of iron oxide nanoparticles, the iron oxide nanoparticles may be synthesized by thermal decomposition of iron oleate as disclosed in Nat. Mater. 2004, 4, 891. However, since the method disclosed in the foregoing document uses only the oleic acid attached in the iron complex, as a surfactant to synthesize the nanoparticles, the quantity of oleic acid is not enough to prepare iron oxide nanoparticles having a size of 4 nm or less. In contrast, the present inventors have successfully synthesized the iron oxide nanoparticles having a size of 4 nm or less by varying conditions for generation of nanoparticles, with different temperature elevation conditions from the patented method in the art. Two different methods have been adopted to control the conditions for generation of nanoparticles.

A first method is to generate a number of nuclei during reaction as described in Examples 6 and 7, wherein nanoparticles having a small size are synthesized to reduce the number of iron atoms adhered to each particle during growth of the particle. This method may control formation of nuclei by regulating a reaction temperature. However, compared to a preferred preparation method of the present invention which includes; reacting an iron complex formed of iron as a central atom and a C4 to C25 carboxylate group bonded thereto in a ligand form; a C4 to C25 fatty acid; and a C4 to C25 aliphatic alcohol or C4 to C25 aliphatic amine at 150 to 350° C. to prepare iron oxide nanoparticles, the foregoing nucleation method through temperature control entails difficulties in controlling the temperature and thus poor reproducibility.

A second method is to synthesize nanoparticles having a small size by controlling a growth rate of nanoparticles, as described in Example 8. In particular, this method delays growth of particles to ensure an intermediate reaction stage in growth of particles. That is, the second method may also adopt temperature control. In contrast, compared to a preferred preparation method of the present invention which includes; reacting an iron complex formed of iron as a central atom and a C4 to C25 carboxylate group bonded thereto in a ligand form; a C4 to C25 fatty acid; and a C4 to C25 aliphatic alcohol or C4 to C25 aliphatic amine at 150 to 350° C. to prepare iron oxide nanoparticles, the foregoing method has disadvantage that it is difficult to control the reaction temperature accurately and so a growth period of particles is not constant during reaction, which in turn, causes problems such as lower yield and less reproducibility.

The following examples are implemented with sodium oleate, oleyl alcohol and diphenylether, which are purchased from TCI; iron chloride (3) hexahydrate, oleic acid (90%), 1-octadecene (90%) and 1,2-hexadecanediol, which are purchased from Aldrich; and oleyl amine which is purchased from Acros. In addition, ethanol and hexane are purchased from Sam-Chun Chemical for use.

TEM is measured by JEOL-2010, XRD is measured by Rigaku Ka, VSM (Vibrating Sample Magnetometer) is measured by VSM-PPMS, and M-T relationship is measured by VSM while raising a temperature by 5K/min.

An iron oleate complex ('iron oleate') used herein is the one prepared by reacting sodium oleate with $FeCl_3$ according to the method disclosed in J. Park et al., Nat. Mater. 2004, 4, 891. More particularly, 10.8 g of iron chloride hexahydrate and 36.5 g of sodium oleate are mixed in 60 mL of water, 80 mL of ethanol and 140 mL of hexane, followed by reaction of the mixture at 60° C. for 4 hours under strong agitation. From a reaction product having two separate phases, the transparent lower phase is removed through a separation funnel. The remaining brown organic phase is mixed with water and then the lower water phase is removed again. The water-soluble salt in the organic phase is eliminated by the washing process. The foregoing washing processes are repeated three times. The organic solution is subjected to evaporation of the hexane, resulting in iron oleate complex.

With regard to analysis of the products in the following examples and comparative examples, the accompanying drawings are as follows:

FIG. 1 shows transmission electron microscopy (TEM) images of 3 nm-size iron oxide nanoparticle synthesized by a method described in Example 1, more particularly; (a) a TEM image; (b) a TEM image in a wide range; (c) a high resolution-transmission electron microscopy (HR-TEM) image; and (d) a selected area electron diffraction (SAED) pattern. FIG. 2 shows an X-ray diffraction (XRD) spectrum of 3 nm-size nanoparticles synthesized by a method described in Example 1. FIG. 3 shows a TEM image of 2.3 nm-size iron oxide nanoparticles synthesized by a method described in Example 2. FIG. 4 shows a TEM image of 1.8 nm-size iron oxide nanoparticles synthesized by a method described in Example 3. FIG. 5 shows a TEM image of 3.3 nm-size iron oxide nanoparticles synthesized by a method described in Example 4. FIG. 6 shows a TEM image of 3.5 nm-size iron oxide nanoparticles synthesized by a method described in Example 5. FIG. 7 shows a TEM image of 1.6 nm-size iron oxide nanoparticles synthesized by a method described in Example 6. FIG. 8 shows a TEM image of 2.4 nm-size iron oxide nanoparticles synthesized by a method described in Example 7. FIG. 9 shows a TEM image of 3.5 nm-size iron oxide nanoparticles synthesized by a method described in Example 8. FIG. 10 shows a TEM image of 2.3 nm-size iron oxide nanoparticles synthesized by a method described in Example 9. FIG. 11 of (a) shows a TEM image of 2.7 nm-size iron oxide nanoparticles synthesized by a method described in Example 10; (b) shows a TEM image of iron oxide nanoparticles synthesized by a method described in Comparative Example 1; and (c) shows a TEM image of iron oxide nanoparticles synthesized by a method described in Comparative Example 2. FIG. 12 of (a) shows M-H graphs at 5K and 300K, respectively, of 3 nm-size nanoparticles synthesized by the method described in Example 1; (b) shows variation in M-H graph at 300K of nanoparticles with particle size; (c) shows zero field cooling and field cooling M-T graphs of 2.3 nm-size nanoparticles synthesized by the method described in Example 2, respectively; (d) shows an M-T graph of 3 nm-size nanoparticles synthesized by a method described in Example 1; (e) shows an M-T graph of 12 nm-size nanoparticles synthesized by a method described in Comparative Example 3; (f) shows M-H graphs at 5K and 300K, respectively, of 1.6 nm-size nanoparticles synthesized by the method described in Example 6; (g) shows an M-T graph of the nanoparticle in Example 6; and (h) shows M-H graphs at 5K and 300K, respectively, of 2.3 nm-size nanoparticles synthesized by the method described in Example 9. FIG. 13 illustrates a distribution of number-average hydrodynamic diameters (number-average of 11.8 nm) of 3 nm-size nanoparticles, which are dispersed in water by using PEG-phosphate (PO-PEG) according to the method described in Example 13. FIG. 14 shows MRI phantom T1 image of dispersions which are prepared by primarily modifying the surface of iron oxide nanoparticles with PEG-phosphate (PO-PEG) and phospholipid PEG, respectively, with particle size, and then secondarily dispersing the surface-modified nanoparticles in water; in particular, in the case where using PO-PEG to treat the nanoparticles having a size of 2.3 nm, 3 nm and 4 nm, respectively, they are each indicated as 2.3 P, 3 P and 4 P; likewise, in the case where using phospholipid-PEG to treat the foregoing nanoparticles, they are each indicated as 2.3 L, 3 L, 4 L and 7 L. FIG. 15 shows cell phantom MRI results of 3 nm-size nanoparticles and 12 nm-size nanoparticles, respectively; in particular, (a) shows cell phantom MR image of 3 nm-size nanoparticles; and (b) shows cell phantom MR image of 12 nm-size nanoparticles. FIG. 16 shows clear contrast images of jugular veins, carotid arteries and aortic arch, which are obtained using the inventive nanoparticles, as compared to a gadolinium complex, Gadovist® (Bayer Schering Co.); in particular, (a) shows in vivo MRI vascular contrast image, using 3 nm-size nanoparticles; and (b) shows in vivo MRI vascular contrast image using Gadovist®. FIG. 17 shows a TEM image of 4 nm-size iron oxide nanoparticles synthesized by a method described in Example 20. FIG. 18 illustrates MTT assay results of MCF-7 cells using hydrophilic-modified iron oxide nanoparticles according to Example 21.

FIG. 19 illustrates molecular weight assay results of iron oxide nanoparticles by means of MALDI-TOF according to Example 22, FIG. 20 shows a TEM image of 12 nm-size iron oxide nanoparticles synthesized by a method described in Comparative Example 3, FIG. 21 shows a TEM image of 12 nm-size iron oxide nanoparticles synthesized by a method described in Comparative Example 4, FIG. 22 shows a TEM image of 7 nm-size iron oxide nanoparticles synthesized by a method described in Comparative Example 5, FIG. 23 shows a TEM image of 4 nm-size iron oxide nanoparticles, which were encapsulated to form an aggregate, followed by negative staining, according to the method described in Comparative Example 6, and FIG. 24 shows a TEM image of 6 nm-size iron oxide nanoparticles synthesized by Comparative Example 7, and FIG. 25 shows enhanced MRI vascular contrast images using the 3-nm nanoparticles capped by glucose 6-phosphate, described in Example 17.

EXAMPLE 1

Synthesis of 3 nm-Size Iron Oxide Nanoparticles 1.8 g (2 mmol) of iron oleate, 0.57 g (2 mmol) of oleic acid and 1.61 g (6 mmol) of oleyl alcohol were mixed with 10 g of diphenylether and placed in a round-bottom flask. Vapor was removed from the flask by vacuuming at 80° C. for 1 hour, then, an argon gas was fed into the flask to make an inert environment. After reacting in the flask while raising the temperature to 250° C. with 10° C./min, the reaction material becomes black during the reaction. After raising the temperature to 250° C., the reaction was continued for 30 minutes, resulting in 3 nm-size nanoparticles (FIGS. 1 and 2). After the reaction the product was rapidly cooled and then washed with excess acetone. After washing, the resulting precipitate was dispersed in an organic solvent such as chloroform or hexane.

EXAMPLE 2

Synthesis of 2.3 nm-Size Iron Oxide Nanoparticles

The synthesis of 2.3 nm-size nanoparticles was performed by thermal decomposition under the same conditions as described in Example 1, after mixing 0.9 g (1 mmol) of iron oleate and 3.22 g (12 mmol) of oleyl alcohol with 10 g of diphenylether, without addition of oleic acid.

EXAMPLE 3

Synthesis of 1.8 nm-Size Iron Oxide Nanoparticles 1.8 nm-size nanoparticles were synthesized by mixing 0.9 g (1 mmol) of iron oleate and 3.22 g (12 mmol) of oleyl alcohol with 10 g of diphenylether, without addition of oleic acid, followed by raising a temperature to 200° C. with a temperature elevation rate of 20° C./min and conducting the reaction at 200° C. for 30 minutes. The other conditions are substantially the same as described in Example 1.

EXAMPLE 4

Synthesis of 3.3 nm-Size Nanoparticles Using 1-Octadecene

Nanoparticles were synthesized by mixing 1.8 g of iron oleate, 0.57 g of oleic acid and 1.6 g of oleyl alcohol with 10 g of 1-octadecene, followed by raising a temperature to 250° C. with a temperature elevation rate of 10° C./min and growing particles at 250° C. for 30 minutes. The other conditions are substantially the same as described in Example 1.

EXAMPLE 5

Synthesis of 3.5 nm-Size Nanoparticles Using Oleyl Amine

Nanoparticles were synthesized by mixing 1.8 g of iron oleate, 0.57 g of oleic acid and 1.6 g of oleyl amine with 10 g of diphenylether, followed by raising a temperature to 250° C. with a temperature elevation rate of 10° C./min and growing particles at 250° C. for 30 minutes. The other conditions are substantially the same as described in Example 1.

EXAMPLE 6

Preparation of 1.6 nm-Size Iron Oxide Nanoparticles

With reference to known synthetic method (Nature Mater. 3(2004), 891), very small iron oxide nanoparticles were synthesized by preventing the growth rate of particles. The synthesized particles were centrifuged to result in very small iron oxide nanoparticles. For nanoparticle synthesis through thermal decomposition of iron oleate, a synthesis temperature is generally 320° C. and particles are rapidly grown at this temperature. On the other hand, energy for growing particles is not sufficiently provided at 300° C., thus the growth rate decreases (that is, the growth of particles). Consequently, nanoparticles having a very small size generated during growth at 300° C. could be obtained, although which cannot be yielded during reaction at 320° C.

After mixing 1.8 g (2 mmol) of iron oleate (Fe-oleate) and 0.57 g (2 mmol) of oleic acid with 10 g of 1-octadecene, the mixture was placed in a round-bottom flask and vapor was removed from the flask by vacuuming at 80° C. for 1 hour. Then, an argon gas was fed into the flask to make an inert environment. Next, after raising the temperature to 300° C. with 3.3° C./min, reaction was conducted at 300° C. for 30 minutes, followed by rapidly cooling the reaction product to room temperature. Following this, the cooled product was subjected to precipitation by adding ethanol thereto at room temperature, resulting in 1.6 nm-size iron oxide.

EXAMPLE 7

Preparation of 2.4 nm-Size Iron Oxide Nanoparticles 2.4 nm-size iron oxide nanoparticles were synthesized by preventing the growth rate of nanoparticles as described in Example 6.

More particularly, after mixing 1.8 g (2 mmol) of iron oleate (Fe-oleate) and 0.57 g (2 mmol) of oleic acid with 10 g of 1-octadecene, the mixture was placed in a round-bottomed flask and vapor was removed from the flask by vacuuming at 80° C. for 1 hour. Then, an argon gas was fed into the flask to make an inert environment. Next, after raising the temperature to 300° C. with 3.3° C./min, reaction was conducted at 300° C. for 35 minutes, followed by rapidly cooling the reaction product to room temperature. Following this, the cooled product was subjected to precipitation by adding ethanol thereto at room temperature, resulting in 2.4 nm-size iron oxide.

EXAMPLE 8

Preparation of 3.5 nm-Size Iron Oxide Nanoparticles

With reference to known synthetic method (Nature Mater. 3(2004), 891), iron oxide nanoparticles having a small size were synthesized through lowering the temperature to produce much more nuclei. Since the nucleation temperature during thermal decomposition of Fe-oleate was about 270° C., reaction materials remained longer at the foregoing temperature of 270° C., to thereby facilitate generation of nuclei in large quantities. The reason for this is that, if numerous nuclei are formed, the number of iron atoms adhered to each particle may be reduced, thus the size of each the particle may decreases.

After mixing 1.8 g (2 mmol) of iron oleate (Fe-oleate) and 0.57 g (2 mmol) of oleic acid with 10 g of 1-octadecene, the mixture was placed in a three-neck round-bottom flask, and heated to 270° C. under an inert atmosphere and stayed therein for 20 minutes to perform synthesis at the same temperature. After nucleation, the temperature was raised to 318° C. as a growth temperature of particles to inhibit further reaction and then stayed at the same temperature, that is, 318° C. for 10 minutes to perform synthesis, thereby resulting in 3.5 nm-size nanoparticles.

EXAMPLE 9

Synthesis of 2.3 nm-Size Iron Oxide Nanoparticles

A solution comprising 0.64 g of oleic acid, 0.59 g of 1,2-hexadecanediol and 15.81 g of diphenylether was purified by removing impurities after vacuuming it at about 70° C. for 1 hour. Then, an argon gas was fed thereto until an inert environment is formed and then stopped. 0.3 ml of iron pentacarbonyl was injected thereto. By raising the temperature to 250° C. with a temperature elevation rate of 3.3° C./min and conducting reaction at 250° C. for 30 minutes, nanoparticles having a size of 2.3 nm were prepared. The other conditions are substantially the same as described in Example 1.

EXAMPLE 10

Particle Size and Distribution Depending Upon Temperature Elevation Rate

After mixing 1.8 g of iron oleate, 0.57 g of oleic acid and 1.6 g of oleyl alcohol with 10 g of diphenylether, a temperature was raised to 250° C. with a temperature elevation rate of 20° C./min and the mixture reacted and nanoparticles was grown at 250° C. for 30 minutes. As a result, uniform nanoparticles having a size of 2.7 nm were synthesized. The other conditions are substantially the same as described in Example 1.

EXAMPLE 11

Physico-Chemical Properties of the Prepared Iron Oxide Nanoparticles

Using a vibrating sample magnetometer (VSM), magnetic property of the nanoparticles was measured. FIG. 12 shows magnetization-magnetic field (M-H) graphs of nanoparticles having different sizes of 1.6, 2.3, 3 and 12 nm, which were synthesized in the foregoing examples. More particularly, in FIG. 12, (a) shows M-H graphs at 5K and 300K, respectively, of 3 nm-size nanoparticles synthesized by the method described in Example 1; (b) shows variation in M-H graph at 300K, of nanoparticles with particle size; (c) shows zero field cooling and field cooling M-T graphs of 2.3 nm-size nanoparticles synthesized by the method described in Example 2, respectively; (d) shows an M-T graph of 3 nm-size nanoparticles synthesized by a method described in Example 1; (e) shows an M-T graph of 12 nm-size nanoparticles synthesized by a method described in Comparative Example 3; (f) shows M-H graphs at 5K and 300K, respectively, of 1.6 nm-size nanoparticles synthesized by the method described in Example 6; (g) shows an M-T graph of 1.6 nm nanoparticles synthesized by the method described in Example 6; and (h) shows M-H graphs at 5K and 300K, respectively, of 2.3 nm-size nanoparticles synthesized by the method described in Example 9.

Referring to FIG. 12, the 12 nm-size iron oxide nanoparticles at 5K are ferrimagnetic to exhibit coercivity and remanent magnetization. 3 nm-size iron oxide nanoparticles are also ferrimagnetic to exhibit a little coercivity as well as remanent magnetization. However, the 2.3 nm-size nanoparticles neither show such remanent magnetization nor coercivity at the temperature. That is, these nanoparticles remain in a paramagnetic state until the temperature of 5K. This is an unexpected case in magnetic nanoparticles having super-paramagnetic properties. The foregoing conditions may be clearly identified from a magnetization-temperature (M-T) graph and, for instance, it can be seen that a blocking temperature is 200K for the 12 nm-size nanoparticles and 10K for the 3 nm-size nanoparticles, however, the blocking temperature of the 2.5 nm nanoparticles is not observed even at 5K. The blocking temperature means a transition temperature, at which physical properties such as super-paramagnetic, ferromagnetic and/or ferrimagnetic properties are exchanged, and may be proportional to the volume of particles. Accordingly, when the particle size is decreased, the blocking temperature may also be lowered. For instance, if the particle size is decreased to 3 nm or less, the blocking temperature does not appear even at 5K. As a result, it can be seen that the 3 nm-size particle is paramagnetic or has paramagnetic-like physical properties. Such characteristic was firstly discovered in iron oxide nanoparticles having a ferrite structure and, since it is similar to paramagnetic property, is referred to as 'pseudo-paramagnetic property' to be distinguishable from super-paramagnetic property. Since the iron oxide nanoparticles having a small size of 3 nm or less are mostly super-paramagnetic nanoparticles and/or have disordered spins on the surface thereof, these particles may look like paramagnetic. More specifically, although the foregoing nanoparticles are not paramagnetic, they show paramagnetic-like behavior, thus being pseudo-paramagnetic.

For assaying, M-H graphs at room temperatures were overlapped (FIG. 12b). It can be seen that magnetization is reduced with decreasing particle size. The reason for this may be presumed that, when the particle is smaller, anisotropic energy is decreased, which in turn, allows high occurrence of so-called Neel relaxation, and overall particles has low magnetization to reduce Zeeman energy, thereby increasing thermal fluctuation. However, it is surprisingly found that a difference in magnetic properties is considerably great between 3 nm particle and 2.3 nm particle, in spite of a small variation in size. The foregoing result may be interpreted by spin-canting effects (J. M. D. Coey, Phys. Rev. Lett. 1971, 27, 1140). For instance, magnetic nanoparticles generally have lower magnetization than in a bulk state. The reason for this is that: surface atoms are under a different environment from bulk atoms, therefore, a spin direction of the surface atoms has a different angle from bulk atoms, which in turn, lower overall spin angle and thus degrades magnetization. This refers to the spin-canting effects described above. Alternatively, Linderoth has estimated a thickness of the spin-canting surface to about 0.9 nm (S. Lindroth et al., J. Appl. Phys. 1994, 75, 6583). According to the foregoing, a 2.3 nm sized nanoparticle may include about 1.0% of core portion in relation to a total volume of the particle, which is not influenced by spin-canting effects.

On the other hand, a 3 nm-sized nanoparticle may include about 6.4% of core portion in the particle. Consequently, it may be considered that a different in magnetization is relatively great.

According to Lindroth's calculation, 1.6 nm-size nanoparticle, of which the almost entire portion is influenced by a spin-canting surface, exhibits typical paramagnetic properties wherein an M-T relationship is linear at room temperature (FIG. 12f). In addition, it can be seen that a large-scale magnetic field is not saturated up to large magnetic field at 5K.

Even through the nanoparticles of the present invention are substantially iron oxide nanoparticles having a ferrite structure (FIG. 2), they have paramagnetic or pseudo-paramagnetic property rather than super-paramagnetic. Accordingly, the foregoing nanoparticles may be highly useful to be used as a MRI T1 contrast agent.

EXAMPLE 12

Hydrophilic Modification of Iron Oxide Nanoparticles Using Phospholipid-PEG 10 mg of the iron oxide nanoparticles having a size of 3 nm prepared in Example 1 was dispersed in 10 ml of chloroform, and then, 10 mg of phospholipid-PEG {1,2-distearyl-sn-glycero-3-phosphoethanol amine-N[methoxy (polyethyleneglycol-2000)]} was added to the dispersion solution. After agitating, the chloroform was slowly evaporated, followed by adding water and finally a well dispersed aqueous iron oxide nanoparticle colloidal was resulted. The hydrodynamic diameter of the hydrophilic nanoparticle was 15 nm, measured by DLS (dynamic light scattering).

EXAMPLE 13

Hydrophilic Modification of Iron Oxide Nanoparticles Using PEG-Phosphate (PO-PEG)

0.15 g of $POCl_3$ and 6 g of polyethyleneglycol methyl ether (Mn:2000) were fed to 7 ml of a tetrahydrofuran (THF) solution and agitated for 4 hours. PO-PEG was obtained after removing THF therefrom. 10 mg of the 3 nm iron oxide nanoparticles having oleate on the surface prepared in Example 1 and 100 mg of PO-PEG were mixed in ethanol, sealed, and agitated at 70° C. for 4 hours, to exchange ligands thereof. The resulting product was washed with N-hexane three times and, after evaporating the ethanol portion, water was added to the residue to disperse the same, thus obtaining colloidal particles having a hydrodynamic diameter of 11.8 nm (FIG. 13).

EXAMPLE 14

MR in Vitro Relaxation of Hydrophilic-Modified Iron Oxide Nanoparticles

In order to determine MR contrast ability of the hydrophilic iron oxide nanoparticle colloids, hydrophilic-modified prepared by the way of Examples 13 and 17, and Comparative Example 6, respectively, several phantoms with concentrations of 0.5, 0.25, 0.13, 0.063, 0.031, 0.016, 0.0078 and 0.0039 mg/ml were prepared using the iron oxide nanoparticles having different sizes of 1.6 nm (Example 6), 2.4 nm (Example 7), 3 nm (Example 1), 4 nm (Example 20) and 7 nm (Comparative Example 5), respectively. 1.5 T MR image was obtained using an MR scanner (GE Health Care, Signa Excite) equipped with a head coil. A T1 value was obtained by means of IR-FSE sequence with the following parameters: TR/TE/T1=4000 ms/8.4 ms/50 to 4000 ms. A T2 value was obtained by means of CPMG sequence with the following parameters: TR/RE=5000 ms/16 to 200 ms.

For 4.7 T MR image, a BGA12 gradient coil (Biospec 47/40, Bruker Biospin MRI GmbH) was used to analyze relaxation performance. More particularly, after analyzing iron content of an iron oxide-PLGA nano-capsule powder by ICP-AES, this powder was subjected to measurement at different concentrations of 2, 1, 0.5, 0.25 and 0.125 mg/l in 0.01M PBS (phosphate buffer saline, pH7.4). T2 relaxation time was measured by means of multi slice-multi echo (MSME) pulse sequence, wherein the parameters used herein may be as follows:

TR (repetition time)=10,000 ms; TE (Echo time)=8 to 2048 ms (256 times with 8 ms intervals); FOV=60×40 mm; Resolution=0.234×0.156 mm/pixel; slice thickness=1 mm; number of acquisition=1; matrix×size=128×128.

The following Table 1 shows r1, r2 and their ratio therebetween of nanoparticles having different sizes at 1.5 T and 4.7 T. Referring to Table 1, 1.5 Tesla phantom MRI relaxation values depending upon size of nanoparticle may be offered. The greatest r1 value is near 7 nm but a difference between r1 values is not so great. On the contrary, when the particle size is decreased, r2 value is considerably reduced. As a result, r2/r1 may also be greatly decreased. For instance, 1.6 nm-size nanoparticles may have a very small r2/r1, that is, about 1.47 in a magnetic field of 1.5 T. Small r2/r1 demonstrates that the corresponding nanoparticles are suitable to be used as T1 MRI contrast agent. Further, referring to Comparative Example 6 in Table 1, it can be seen that, even when a diameter of each iron oxide nanoparticle is 4 nm, r2/r1 is excessively increased where a plurality of nanoparticles are aggregated (FIG. 23), thus being not preferable for T1 contrast agent.

TABLE 1

| Surface modification | Ligand | Average particle size (preparation) | r1 | r2 | r2/r1 | Magnetic field (T) |
|---|---|---|---|---|---|---|
| Example 13 | PO-PEG | 1.6 nm (Example 6) | 0.146 | 0.215 | 1.47 | 1.5 |
| Example 13 | PO-PEG | 2.4 nm (Example 7) | 0.360 | 1.75 | 4.86 | 1.5 |
| Example 13 | PO-PEG | 3 nm (Example 1) | 1.22 | 6.31 | 5.17 | 1.5 |
| Example 13 | PO-PEG | 4 nm (Example 20) | 1.78 | 14.9 | 8.37 | 1.5 |
| Example 17 | Glucose 6-phosphate | 3 nm (Example 1) | 3.5 | 14.8 | 4.2 | 4.7 |
| Example 13 | PO-PEG | 7 nm (Comparative example 5) | 4.28 | 44.1 | 10.3 | 1.5 |
| Example 13 | PO-PEG | 12 nm (Comparative example 3) | 1.63 | 70.9 | 43.5 | 1.5 |
| Comparative example 6 | PLGA | 4 nm (hydrodynamic diameter: 117 nm) (example 20) | 0.095 | 99.45 | 1053.3 | 4.7 |

EXAMPLE 15

MR Imaging of Cell

In vitro T1 weighted MR images of MCF-7 cells incubated with various concentrations of the nanoparticles (0, 25, 100 μg Fe/mL) were obtained on a 1.5 T MR scanner. Significant T1 signal enhancement was observed for the cells labeled with 25 and 100 μg Fe/mL of 3 nm nanoparticles capped by PO-PEG while non-labeled cells were not brightened (FIG. 15a). Although nanostructured materials are usually clustered in the endosome, 3 nm nanoparticles provide T1 contrast effect not only in deionized water but also in the cellular environment resulting from their low volume anisotropy. In contrast, in the cell phantom T1 weighted MR image, the cells labeled with 12 nm-sized particles showed much less signal enhancement; even they were darkened at the high concentration (FIG. 15b). The attenuated T1 signal of cell incubated with the 12 nm-sized iron oxide nanoparticles seems to result from the susceptibility effect derived from the strong magnetic moment of aggregates of the large-sized magnetic nanoparticles.

EXAMPLE 16

MR In Vivo Imaging of the 3 nm Iron Oxide Nanoparticles PO-PEG on the Surface

Dynamic time-resolved MR angiography and 3d-FLASH images of rats were acquired using a wrist coil on a 3 T MRI scanner before and after the injection of 3 nm iron oxide nanoparticles capped by PO-PEG, prepared according to example 13 (dose: 2.5 mg Fe/kg). The pre-contrast images were subtracted from post-contrast images, and the resulting images were reconstructed using maximum intensity projection (MIP) protocol with OsriX (Version 3.8.1; 32 bit; OsiriX foundation, Geneva). Dynamic time-resolved MR angiography was obtained with an interpolated temporal resolution of 1.25 second and the following parameters: flip angle=20, ETL=1, TR=3.1 ms, TE=1.13 ms, field of view FOV=75×140 mm$^2$, matrix=256×106, slice thickness/gap=2.5 mm/0 mm, and NEX=1. The imaging parameters of 3d-FLASH are as follows: flip angle=25, ETL=1, TR=25 ms, TE=5.1 ms, field of view FOV=110×65 mm$^2$, matrix=256×169, slice thickness/gap=1.0 mm/0 mm, and NEX=2.

FIG. 16a blood vessels were brightened on the T1 weighted MR images, demonstrating that the 3 nm nanoparticles can enhance T1 relaxation in the circulating system. The bright signal of blood vessel can be maintained for 1 h on dynamic time-resolved MR angiography (not shown in FIG. 16), showing that the 3 nm nanoparticles can be used for T1 enhanced blood pool MRI contrast agent.

Blood pool imaging is important in clinical MR imaging because it can detect the myocardial infarction, renal failure, atherosclerotic plaque, thrombosis, and angiogenesis of tumor cells. Long-term blood pool imaging is beneficial for steady-state imaging, which is critical to obtain high-resolution images. For example, pulmonary artery imaging could clearly be obtained by the steady-state imaging using USPIO (Ultra Small Superparamagnetic iron oxide)s. The 3 nm nanoparticles can be good T1 contrast agent for steady-state imaging because they have a long blood half-life derived from their optimal particle size.

The particles should not be so large to avoid uptake by the reticuloendothelial system and should not be so small to keep the particles from being excreted through the kidney. In contrast to the 3 nm nanoparticles, gadolinium complex Gadovist (Bayer Schering Pharma), which is a commonly used T1 MRI contrast agent, has a short blood half-life. Immediately after the injection of Gadovist, in vivo MR image exhibited high contrast effect due to its high relaxivity, but the bright signal vanished rapidly in 2 minutes (FIG. 16b).

EXAMPLE 17

Hydrophilic Modification of Iron Oxide Nanoparticles Using Monosaccharide Phosphate and MR In Vivo Imaging Iron oxide nanoparticles capped by oleic acid on the surface were prepared by the method of example 1.

100 mg of 3 nm iron oxide nanoparticles were dispersed in 8 ml of THF (tetrahydrofuran) and mixed with aqueous solution of 200 mg of glucose 6-phosphate sodium salt in 2 ml of water. The mixed solution was agitated and reacted at 60° C. for 4 hr. After cooling, upper phase of THF of the mixture solution was separated and water was added to the lower phase of iron oxide nanoparticles capped by glucose 6-phosphate on the surface to prepare a stable colloid of iron oxide nanoparticles.

The hydrodynamic diameter of the nanoparticles having glucose 6-phosphate on the surface was 3.8 nm, measured by dynamic light scattering method (Malvern Zetasizer Nano ZS).

MR imaging using the 3 nm nanoparticles capped by glucose 6-phosphate was performed according to example 16.

As shown in FIG. 25 blood vessels were brightened on the T1 weighted MR imaging. The bright signal of blood could be maintained for 2 hour, but the bright signal was not shown after 24 hours. This means the composition of 3 nm nanoparticles capped by glucose 6-phosphate can be a good MR blood pool agent.

EXAMPLE 18

Hydrophilic Modification of Iron Oxide Nanoparticles Using Citric Acid

Iron oxide nanoparticles capped by oleic acid on the surface were prepared by the method of example 1.

100 mg of 3 nm iron oxide nanoparticles were dispersed in 8 ml of THF (tetrahydrofuran) and mixed with aqueous solution of 400 mg of sodium citrate in 2 ml of water. The mixed solution was agitated and reacted at 60° C. for 4 hr. After cooling, upper phase of THF of the mixture solution was separated and water was added to the lower phase of iron oxide nanoparticles capped by citric acid on the surface to prepare a stable colloid of iron oxide nanoparticles.

The hydrodynamic diameter of the nanoparticles having citric acid on the surface was 10 nm, measured by dynamic light scattering method (Malvern Zetasizer Nano ZS).

EXAMPLE 19

Hydrophilic Modification of Iron Oxide Nanoparticles Using Betaine.

Iron oxide nanoparticles capped by oleic acid on the surface were prepared by the method of example 1.

150 mg of 3 nm iron oxide nanoparticles were dispersed in 25 ml of n-hexane and mixed with 600 mg of betaine (2-(trimethyl azaniumyl)acetate hydrochloride) in 25 ml of ethanol. The mixed solution was agitated and reacted at 50° C. for 8 hr. After cooling, the ligand exchanged nanoparticles were separated from the solvent by centrifugation at 3000 rpm for 10 min. Water was added to the ligand exchanged nanoparticles Betaine to prepare a stable colloid of iron oxide nanoparticles.

The hydrodynamic diameter of the nanoparticles having betaine on the surface was 7 nm, measured by dynamic light scattering method (Malvern Zetasizer Nano ZS).

EXAMPLE 20

Synthesis of 4 nm-Size Iron Oxide Nanoparticles

With reference to the method described in Example 6, 4 nm-size iron oxide nanoparticles were synthesized through control of particle growth rate. More particularly, 4 nm-size nanoparticles were synthesized as follows: after mixing 1.8 g of iron oleate and 0.57 g of oleic acid with 10 g of 1-octadecene, a temperature was raised to 318° C. with a temperature elevation rate of 10° C./min, followed by conducting reaction at 318° C. for 30 minutes and then rapidly cooling the reaction product to room temperature. Following this, the cooled product was subjected to precipitation by adding ethanol thereto at room temperature, resulting in 4 nm-size iron oxide.

EXAMPLE 21

MTT Assay Experiment of Hydrophilic-Modified Iron Oxide Nanoparticles

Under a wet atmosphere 37° C. and with 5% $CO_2$ concentration, human breast cancer cell lines, that is, MCF-7 cells were grown on a Dulbecco's modified eagle's medium (DMEM, Welgene) containing 10% fetal bovine serum (FBS) and 1% penicillin/streptomycin (100 U/ml and 100 μg/ml, respectively, Gibco).

For observation of intracellular intake, the MCF-7 cells were incubated on eight (8)-well chamber slide, followed by mixing the cultured cells with each of 3 nm-size and 12 nm-size iron oxide nanoparticles, which were surface-modified with PO-PEG. After 24 hours, the cells were washed with PBS and then fixed using 4% para-formaldehyde. Fluorescent images were obtained by a confocal laser scanning microscope (LSM 510, Carl Zeiss, Germany).

In order to assay survival and growth of cells in the presence of nanoparticles, analysis using 3-[4,5-dimethyl-thialzol-2-yl]-2,5-diphenyltetrazolium bromide (MTT, Sigma) was performed. For this purpose, MCF-7 cells were grown on 200 μL medium for 1 day. The grown cells were mixed with each of 3 nm-size and 12 nm-size nanoparticles capped by PO-PEG on the surface having different concentrations (e.g., 0, 1.56, 3.13, 6.25, 12.5, 25, 50 and 100 μg Fe/mL). After the mixture was cultured overnight, the cultured material was mixed with a medium containing 0.1 mg/mL of MMT for 1 hour. Following this, the medium was removed and the precipitated formazan was dissolved in DMSO. Using a VerseMax™ microplate reader (Molecular Devices), absorbance at 540 nm was detected to identify cell viability.

Following FIG. 18, both nanoparticles with 4 nm and 10 nm show about 100% of MCF-7 cell viability up to 100 mg Fe/ml. This means both nanoparticles capped by PO-PEG don't have cell toxicity up to the concentration.

EXAMPLE 22

MALDITOF Mass Spectrometry 10 mg/ml of iron oxide nanoparticles and 10 mg/ml of 9-nitroanthracene used as a matrix were dissolved in chloroform. The nanoparticles and 9-nitroanthracene were blended in a relative ratio of 1:100 and only a droplet of the mixture was added to an LDI substrate and then evaporated into the atmosphere. The substrate was placed in an MALDI-TOF spectrometer (Voyager-DETM STR Biospectrometry Workstation, Applied Biosystems Inc.), followed by laser irradiation to measure a mass of the nanoparticles in the range of 500 to 300,000 Da in a linear model and cation detection model, respectively. FIG. 19 shows the result of molecular weight of the nanoparticles by MALDI-TOF. (a) is a TEM image of 1.6 nm-size iron oxide nanoparticles; (b) shows assay results of the 1.6 nm-size iron oxide nanoparticles through MALDI-TOF, wherein the nanoparticles have a molecular weight of 9,000 Da; (c) is a TEM image of 2.4 nm-size iron oxide nanoparticles; (d) shows assay results of the 2.4 nm-size iron oxide nanoparticles through MALDI-TOF, wherein the nanoparticles have a molecular weight of 65,000 Da; and (e) shows mass assay results of a core part of the 1.6 nm-size iron oxide nanoparticles through thermogravimetric analysis (TGA), wherein the core mass is 35.8% and this means that each 1.6 nm-size particle has a core fraction of 35.8%, therefore, a molecular weight of the core is 3,330 Da.

EXAMPLE 23

Hydrophilic Modification of Iron Oxide Nanoparticles Using Glucose 6-Phosphate-Ethanolamine

EXAMPLE 23-1

Synthesis of Glucose 6-Phosphate-Ethanolamine 1 g of Glucose 6-phosphate sodium salt, 0.68 g of EDC (1-ethyl-3-[3-dimethylaminopropyl]carbodiimide hydrochloride) and 0.4 g of NHS (N-hydroxysuccinimide) were mixed with 10 ml of MES (2-(N-morpholino)ethanesulfonic acid) buffer solution. The mixed solution was agitated and reacted at 30° C. for 30 min. After reacting, 0.22 ml of ethanolamine(2-aminoethanol) mixed with the solution then reacted at 30° C. for 12 hours. Glucose 6-phosphate-ethanolamine was obtained after removing MES buffer solution.

EXAMPLE 23-2

Hydrophilic Modification of Iron Oxide Nanoparticles Using Glucose 6-Phosphate-Ethanolamine Iron oxide nanoparticles capped by oleic acid on the surface were prepared by the method of example 1.

100 mg of 3 nm iron oxide nanoparticles were dispersed in 10 ml of THF (tetrahydrofuran) and mixed with aqueous solution of 300 mg of Glucose 6-phosphate-ethanolamine in 2 ml of water. The mixed solution was agitated and reacted at 60° C. for 4 hr. After cooling, upper phase of THF of the mixture solution was separated and water was added to the lower phase of iron oxide nanoparticles capped by Glucose 6-phosphate-ethanolamine on the surface to prepare a stable colloid of iron oxide nanoparticles.

The hydrodynamic using the 3 nm nanoparticles capped by Glucose 6-phosphate-ethanolamine on the surface to prepare a stable colloid of iron nanoparticles. The hydrodynamic diameter of the nanoparticles having Glucose 6-phosphate-ethanolamine on the surface was 8 nm, measured by dynamic light scattering method (Malvern Zetasizer Nano ZS).

EXAMPLE 24

Hydrophilic Modification of Iron Oxide Nanoparticles Using Glucose 6-Phosphate-PEG

EXAMPLE 24-1

Synthesis of Glucose 6-Phosphate-PEG 1 g of Glucose 6-phosphate sodium salt, 0.68 g of EDC (1-ethyl-3-[3-dimethylaminopropyl]carbodiimide hydrochloride) and 0.4 g of NHS (N-hydroxysuccinimide) were mixed with 10 ml of MES (2-(N-morpholino)ethanesulfonic acid) buffer solution. The mixed solution was agitated and reacted at 30° C. for 30 min. After reacting, 0.23 ml of diethyl amine mixed with the solution then reacted at 30° C. for 12 hours. After reacting, the solution mixed with EDC activated mPEG-COOH solution which prepared by 17.75 g of mPEG-COOH (Methoxy-Polyethylene glycol-carboxyl, Mn:5000), 1.361 g of EDC and 0.817 g of NHS were mixed with 40 ml of MES buffer solution. The mixed solution was agitated and reacted at 30° C. for 24 hours. After removing the byproduct by dialysis process, the Glucose 6-phosphate-PEG was obtained after removing DIW.

EXAMPLE 24-2

Hydrophilic Modification of Iron Oxide Nanoparticles Using Glucose 6-Phosphate-PEG Iron oxide nanoparticles capped by oleic acid on the surface were prepared by the method of example 1.

100 mg of 3 nm iron oxide nanoparticles were dispersed in 10 ml of THF (tetrahydrofuran) and mixed with aqueous solution of 1 g of Glucose 6-phosphate-PEG in 2 ml of water. The mixed solution was agitated and reacted at 60° C. for 4 hr. After cooling, upper phase of THF of the mixture solution was separated and water was added to the lower phase of iron oxide nanoparticles capped by Glucose 6-phosphate-PEG on the surface to prepare a stable colloid of iron oxide nanoparticles.

The hydrodynamic using the 3 nm nanoparticles capped by Glucose 6-phosphate-PEG on the surface to prepare a stable colloid of iron nanoparticles. The hydrodynamic diameter of the nanoparticles having Glucose 6-phosphate-PEG on the surface was 14 nm, measured by dynamic light scattering method (Malvern Zetasizer Nano ZS).

COMPARATIVE EXAMPLE 1

Particle Size and Distribution Depending Upon Temperature Elevation Rate

After mixing 1.8 g of iron oleate, 0.57 g of oleic acid and 1.6 g of oleyl alcohol with 10 g of diphenylether, a temperature was raised to 250° C. with a temperature elevation rate of 3.3° C./min and the mixture was grown at 250° C. for 30 minutes. As a result, non-uniform nanoparticles including particles having almost 6 nm-size nanoparticles were synthesized. The other conditions are substantially the same as described in Example 1.

COMPARATIVE EXAMPLE 2

Particle Size and Distribution Depending upon Temperature Elevation Rate

After mixing 1.8 g of iron oleate, 0.57 g of oleic acid and 1.6 g of oleyl alcohol with 10 g of diphenylether, a temperature was raised to 250° C. with a temperature elevation rate of 5° C./min and the mixture reacted at 250° C. for 30 minutes. As a result, non-uniform size nanoparticles including particles having almost 6 nm-size nanoparticles were synthesized. The other conditions are substantially the same as described in Example 1.

COMPARATIVE EXAMPLE 3

Synthesis of 12 nm-Size Nanoparticles 12 nm-size nanoparticles were synthesized by the same method as disclosed in J. Park et al., Nat. Mater. 2004, 4, 891. More particularly, after mixing 1.8 g of iron oleate and 0.28 g of oleic acid with 10 g of 1-octadecene, followed by raising a temperature to 318° C. with a temperature elevation rate of 3.3° C./min and reacting and growing nanoparticles at 318° C. for 30 minutes. FIG. 20 shows a TEM image of the synthesized nanoparticles by observation.

COMPARATIVE EXAMPLE 4

Synthesis of Iron Oxide Nanoparticles Using Behenic Acid

In order to inhibit excessive growth of nanoparticles by steric hindering and to try to produce small size particles, a bulky surfactant was used instead of a small fatty acid. Behenic acid having higher steric hindrance than oleic acid was added during synthesis, thus trying to inhibit excessive growth of the nanoparticles.

With regard to the synthesis, 1.8 g of iron oleate and 0.34 g of behenic acid were mixed with 10 g of 1-octadecene, followed by raising a temperature to 318° C. with a temperature elevation rate of 3.3° C./min and reacting the mixture at 318° C. for 30 minutes. As a result, iron oxide nanoparticles having a size of 12 nm were observed and this size is substantially equal to that of nanoparticles obtained using oleic acid with relatively small steric hindrance. From the result, it was confirmed that the size of iron oxide nanoparticles is not controlled by using steric hindrance in the case where thermal decomposition of iron oleate is applied. FIG. 21 is a TEM image of the synthesized nanoparticles by observation.

COMPARATIVE EXAMPLE 5

Synthesis of 7 nm-Size Nanoparticles 7 nm-size nanoparticles were synthesized by mixing 1.8 g of iron oleate and 0.57 g of oleic acid with 10 g of 1-octadecene, followed by raising a temperature to 318° C. with a temperature elevation rate of 5° C./min and reacting the mixture at 318° C. for 30 minutes. FIG. 22 shows a TEM image of the synthesized nanoparticles by observation.

COMPARATIVE EXAMPLE 6

Preparation of Hydrophilic-Modified Capsules Including Aggregation of 4 nm-Size Iron Oxide Nanoparticles After dispersing 40 mg of 4 nm-size iron oxide nanoparticles and 40 mg of poly(lactic-co-glycolic acid) (PLGA) in an ethyl acetate solution, the dispersion was mixed with 4 ml of Pluronic® F127 solution (BASF Corporation, Difunctional Block Copolymer) and agitated, resulting in capsules. As a result of TEM observation (FIG. 23), it was found that several aggregates composed of nanoparticles are present in an encapsulated state. According to measurement through dynamic light scattering (DLS) (Maker: Malven), the nanoparticles have a hydrodynamic diameter (z-average) of 117 nm.

COMPARATIVE EXAMPLE 7

Synthesis Using 1,2-Hexadecanediol 1.8 g of iron oleate, 0.57 g of oleic acid and 1.55 g of 1,2-hexadecanediol were mixed with 10 g, of diphenylether, followed by raising a temperature to 250° C. with a temperature elevation rate of 10° C./min and reacting the mixture at 250° C. for 30 minutes to synthesize the nanoparticles. The other conditions are substantially the same as described in Example 1. As a result of TEM observation, it was found that slightly non-uniform size nanoparticles having a size of 6 nm were synthesized. In the case where the synthesis was performed by replacing oleyl alcohol with 1,2-hexadecanediol having two hydroxyl groups, nanoparticles having a small size of about 4 nm were not obtained, although thermal decomposition could be executed at a low temperature (FIG. 24).

While the present invention has been described with respect to embodiments, specific examples and accompanying drawings, these are only given for overall understanding and the present invention is not particularly limited thereto. Therefore, it will be apparent to those skilled in the art that modifications and variations may be possible from the foregoing.

Accordingly, the spirit of the present invention is not restricted to the foregoing embodiments, various changes and modifications may be included in the scope of the present invention as defined in the appended claims and equivalents thereof.

The invention claimed is:

1. A method for preparation of iron oxide nanoparticles, comprising:
   reacting an iron complex having iron as a central atom and a carboxylate group having 10 to 22 carbon atoms that is bonded to the central atom in a ligand form; a C10 to C22 fatty acid; and a C10 to C22 aliphatic alcohol or C10 to C22 aliphatic amine to prepare iron oxide nanoparticles having an average size of 3.5 nm or less and being paramagnetic or pseudo-paramagnetic at a temperature of 20K or higher, wherein the iron oxide nanoparticle preparation is performed by raising the temperature from room temperature to 200 to 250° C. with a temperature elevation rate of 10° C./m or more, and conducting reaction at 200 to 250° C. for 5 to 60 minutes.

2. The method of claim 1, further comprising dispersing a precipitate in an organic solvent, wherein the precipitate is obtained by cooling and washing the nanoparticles described above.

3. The method of claim 1, wherein the iron complex is iron oleate.

4. The method of claim 1, wherein the fatty acid and aliphatic alcohol are oleic acid and oleyl alcohol, respectively, while the aliphatic amine is oleyl amine.

5. The method of claim 1, wherein the size of iron oxide is controlled by regulating the molar ratio of fatty acid and aliphatic alcohol or aliphatic amine.

* * * * *